(12) United States Patent
Kuramoto et al.

(10) Patent No.: US 9,734,592 B2
(45) Date of Patent: Aug. 15, 2017

(54) MEDICAL IMAGE PROCESSING DEVICE AND METHOD FOR OPERATING THE SAME

(71) Applicant: FUJIFILM Corporation, Tokyo (JP)

(72) Inventors: Masayuki Kuramoto, Ashigarakami-gun (JP); Makoto Sugizaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 15 days.

(21) Appl. No.: 14/963,776

(22) Filed: Dec. 9, 2015

(65) Prior Publication Data

US 2016/0171718 A1 Jun. 16, 2016

(30) Foreign Application Priority Data

Dec. 10, 2014 (JP) .................................. 2014-250227

(51) Int. Cl.
| | |
|---|---|
| G06T 7/40 | (2017.01) |
| A61B 5/00 | (2006.01) |
| G06T 7/00 | (2017.01) |
| G06T 7/90 | (2017.01) |

(52) U.S. Cl.
CPC ............ G06T 7/408 (2013.01); A61B 5/4238 (2013.01); G06T 7/0012 (2013.01); G06T 7/90 (2017.01); G06T 2207/30092 (2013.01)

(58) Field of Classification Search
USPC .................................. 382/128, 162; 348/65
See application file for complete search history.

(56) References Cited

U.S. PATENT DOCUMENTS

| | | | | |
|---|---|---|---|---|
| 5,550,582 A | * | 8/1996 | Takasugi | A61B 1/0638 348/29 |
| 8,111,286 B2 | * | 2/2012 | Inuiya | A61B 1/042 348/164 |
| 8,743,189 B2 | * | 6/2014 | Kitamura | A61B 1/041 348/65 |
| 8,811,676 B2 | * | 8/2014 | Kitamura | G06T 7/0012 382/106 |
| 9,538,902 B2 | * | 1/2017 | Chun | A61B 1/00009 |

(Continued)

FOREIGN PATENT DOCUMENTS

JP 2003-220019 A 8/2003

*Primary Examiner* — Ishrat I Sherali
(74) *Attorney, Agent, or Firm* — Birch, Stewart, Kolasch & Birch, LLP

(57) ABSTRACT

RGB image signals are inputted. A B/G ratio is calculated from the B and G image signals. A G/R ratio is calculated from the G and R image signals. First, second, and third areas are located in a feature space formed by the B/G and G/R ratios. An equal angular magnification process is performed on an angle in a region R1x including a first reference line passing through the second area. An angle expansion process or an angle compression process is performed on an angle in a region R1y located outside the region R1x. An equal radial-coordinate magnification process is performed on a radial coordinate in a region R2x, which includes a second reference line passing through the second area and intersecting the first reference line. A radial-coordinate expansion process or a radial-coordinate compression process is performed on a radial coordinate in a region R2y located outside the region R2x.

15 Claims, 26 Drawing Sheets

(56) References Cited

U.S. PATENT DOCUMENTS

| | | | |
|---|---|---|---|
| 9,545,187 B2 * | 1/2017 | Chun | G06T 5/009 |
| 9,595,085 B2 * | 3/2017 | Kuramoto | G06T 5/009 |
| 9,622,645 B2 * | 4/2017 | Moriya | A61B 1/00009 |
| 2015/0379698 A1 * | 12/2015 | Kuramoto | G06T 5/009 |
| | | | 382/128 |
| 2017/0032539 A1 * | 2/2017 | Kuramoto | A61B 1/0005 |

* cited by examiner

FIG. 21
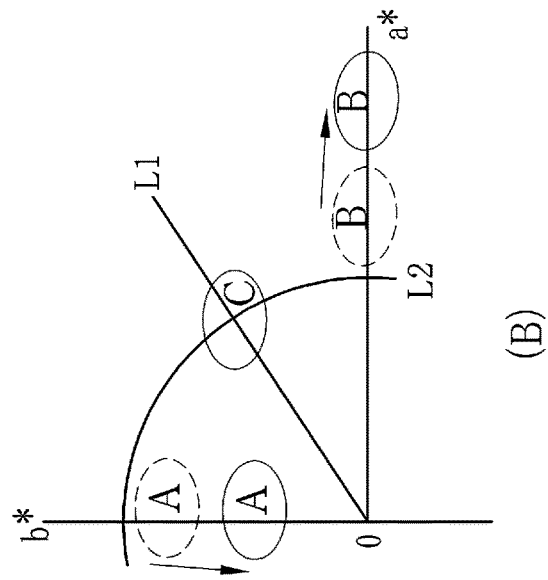
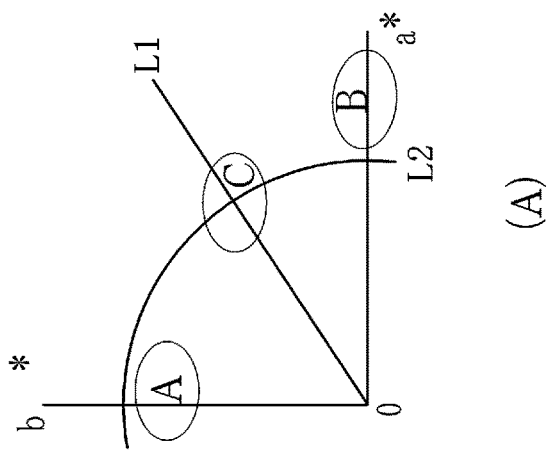

MEDICAL IMAGE PROCESSING DEVICE AND METHOD FOR OPERATING THE SAME

CROSS-REFERENCE TO RELATED APPLICATIONS

The present application claims priority under 35 U.S.C. §119 to Japanese Patent Application No. 2014-250227, filed Dec. 10, 2014. Each of the above application(s) is hereby expressly incorporated by reference, in its entirety, into the present application.

BACKGROUND OF THE INVENTION

1. Field of the Invention

The present invention relates to a medical image processing device that enables displaying a medical image that is a captured image of an object of interest in a body cavity and a method for operating a medical image processing device.

2. Description Related to the Prior Art

In diagnosing stomach cancer, it has been recognized that the onset of the stomach cancer is closely related to the presence of *Helicobacter pylori* (*H. pylori*). In 1994, WHO (the World Health Organization) announced that the *H. pylori* is a carcinogen. The eradiation of the *H. Pylori* infection has been performed to reduce the stomach cancer. After the eradication, whether the eradication has been successful is examined.

Whether a patient is infected or uninfected (not yet infected) with the *H. pylori* is examined by a blood test or by using an endoscope system, which comprises a light source device, an endoscope, and a processor device. In the endoscope system, an image of an object of interest (hereinafter simply referred to as the object) is displayed on a monitor based on RGB image signals generated by capturing an image of the object with an image sensor while the object is irradiated with illumination light from the endoscope. In a case where diffuse redness appears in the image on the monitor, it is diagnosed that there is a high possibility of the presence of the *H. pylori*, which is likely to cause cancer.

It is also known that the presence of the *H. pylori* correlates with IHb (also referred to as the hemoglobin index, which is represented by a G/R ratio between a G image signal and an R image signal) (see Japanese Patent Unexamined Application Publication No. 2003-220019). In this document, the IHb is used as an index for determining whether the eradication of the *H. pylori* infection has been successful. According to this document, in the case where the IHb is greater than a threshold value "59", it is diagnosed that the eradiation of the *H. pylori* infection has not been successful and the *H. pylori* is still present. In the case where the IHb is less than the threshold value "59", it is diagnosed that the *H. pylori* has been eradicated successfully.

In a feature space formed by the B/G ratio (the vertical axis, the ratio between the B image signal and the G image signal) and the G/R ratio (horizontal axis) shown in FIG. 30, the coordinates corresponding to a portion (of the object) uninfected with the *H. pylori* are distributed in an area "A". The coordinates corresponding to a portion (of the object) infected with the *H. pylori* are distributed in an area "B". The coordinates corresponding to a portion (of the object) in which the eradication of the *H. pylori* infection has been successful are distributed in an area "C". The areas "A", "B", and "C" may coexist in the feature space. There are cases where the distinction among the areas "A", "B", and "C" is difficult based only on the value of the G/R ratio (the horizontal axis) representing the IHb. It has been requested to display an image that enables the distinction between the infection of the *H. pylori* and the successful eradication of the *H. pylori*, without using the IHb.

SUMMARY OF THE INVENTION

An object of the present invention is to provide a medical image processing device that produces an image in which uninfection of *H. pylori*, infection of the *H. pylori*, and successful eradication of the *H. pylori* are distinguished from each another and a method for operating a medical image processing device.

An aspect of the present invention provides a medical image processing device comprising an input processing unit, a color information obtaining section, an angle adjuster, and a radial-coordinate adjuster. The input processing unit is configured to perform an input process of a first color image signal. The color information obtaining section is configured to obtain two or more pieces of color information from the first color image signal. The angle adjuster is configured to perform an equal angular magnification process and an angle expansion process or an angle compression process in a feature space formed by the two or more pieces of color information. The feature space includes first, second, and third areas to be observed. In the equal angular magnification process, an angle in a region R1x, which includes a first reference line passing through the second area, is maintained unchanged based on an angle change rate W1x. An angle in a region R1y located outside the region R1x is changed based on an angle change rate W1y greater than the angle change rate W1x in the angle expansion process or based on the angle change rate W1y less than the angle change rate W1x in the angle compression process. The radial-coordinate adjuster is configured to perform an equal radial-coordinate magnification process and a radial-coordinate expansion process or a radial-coordinate compression process. A radial coordinate in a region R2x, which includes a second reference line passing through the second area and intersecting the first reference line, is maintained unchanged based on a radial-coordinate change rate W2x in the equal radial-coordinate magnification process. A radial coordinate in a region R2y located outside the region R2x is changed based on a radial-coordinate change rate W2y greater than the radial-coordinate change rate W2x in the radial-coordinate expansion process or based on the radial-coordinate change rate W2y less than the radial-coordinate change rate W2x in the radial-coordinate compression process.

It is preferred that each of the angle change rate W1x and the radial-coordinate change rate W2x is 1.0.

It is preferred that the angle expansion process or the angle compression process changes each of the angle in the area in the region R1y on one side of the first reference line and the angle in the another area in the region R1y on the other side of the first reference line to be away from the first reference line in an angle direction.

It is preferred that, in a case where an angle θ is defined as an angle from the first reference line, and the angle θ located on one side of the first reference line is defined as a positive angle and the angle θ located on the other side of the first reference line is defined as a negative angle, the region R1x is a range in which the angle θ ranges from "−θ1" that is less than "0" to "+θ2" that is greater than "0". In the region R1x, the angle θ before the equal angular magnification process is equivalent to the angle θ after the equal angular magnification process. The region R1y includes a negative angle range in which the angle θ ranges from "−θ3"

that is less than "−θ1" to "−θ1" and a positive angle range in which the angle θ ranges from "θ2" to "θ4" that is greater than "θ2". In the negative angle range, the angle θ after the angle expansion process or the angle compression process is less than the angle θ before the angle expansion process or the angle compression process. In the positive angle range, the angle θ after the angle expansion process or the angle compression process is greater than the angle θ before the angle expansion process or the angle compression process.

It is preferred that, in a case where the angle θ is greater than "θ4" or less than "−θ3", the angle adjuster maintains the angle θ unchanged based on the angle change rate W1x.

It is preferred that the radial-coordinate expansion process or the radial-coordinate compression process changes each of the radial coordinate in the area in the region R2y on one side of the second reference line and the radial coordinate in the another area in the region R2y on the other side of the second reference line to be away from the second reference line in a radial-coordinate direction.

It is preferred that, in a case where the radial coordinate r corresponding to the first reference line is defined as a radial coordinate rc, the region R2x is a range in which the radial coordinate r ranges from "r1" that is less than "rc" to "r2" that is greater than "rc", and the radial coordinate r before the equal radial-coordinate magnification process is equivalent to the radial coordinate r after the equal radial-coordinate magnification process in the region R2x. The region R2y comprises a small radial-coordinate range in which the radial coordinate r ranges from "r3" that is less than "r1" to "r1" and a large radial-coordinate range in which the radial coordinate r ranges from "r2" to "r4" that is greater than "r2". In the small radial-coordinate range, the radial coordinate r after the radial-coordinate expansion or the radial-coordinate compression is less than the radial coordinate r before the radial-coordinate expansion or the radial-coordinate compression. In the large radial-coordinate range, the radial coordinate r after the radial-coordinate expansion or the radial-coordinate compression is greater than the radial coordinate before the radial-coordinate expansion or the radial-coordinate compression.

It is preferred that, in a case where the radial coordinate r is greater than "r4" or less than "r3", the radial-coordinate adjuster maintains the radial coordinate r unchanged based on the radial-coordinate change rate W2x.

It is preferred the first area is located on one side of the first reference line and the third area is located on the other side of the first reference line.

It is preferred that the first area is located on one side of the second reference line and the third area is located on the other side of the second reference line.

It is preferred that the first color image signal comprises image signals of three colors. It is preferred that the two or more pieces of color information are a first signal ratio between the image signals of the two colors out of the three colors and a second signal ratio between the image signals of the two colors different from the first signal ratio. It is preferred that the feature space is a signal ratio space formed by the first signal ratio and the second signal ratio.

It is preferred that the feature space is anyone of a Cb-Cr space formed by chrominance signals Cr and Cb, which correspond to the two or more pieces of color information, and an ab space formed by color components a* and b*, which correspond to the two or more pieces of color information, of CIE Lab space.

It is preferred that the second area maintains its position in an HS space formed by H (hue) and S (saturation) and the first and third areas move in directions different from each other in each of a hue direction and a saturation direction in the HS space, through the equal angular magnification process and the angle expansion process or the angle compression process, and the equal radial-coordinate magnification process and the radial-coordinate expansion process or the radial-coordinate compression process.

It is preferred that the medical image processing device further comprises a color image signal converter and a brightness adjuster. The color image signal converter is configured to convert the two or more pieces of color information that have been subjected to the equal angular magnification process and the angle expansion process or the angle compression process and the equal radial-coordinate magnification process and the radial-coordinate expansion process or the radial-coordinate compression process, into a second color image signal. The brightness adjuster is configured to adjust a pixel value of the second color image signal based on first brightness information calculated from the first color image signal and second brightness information calculated from the second color image signal.

An aspect of the present invention provides a method for operating a medical image processing device comprising the steps of an input step, a color information obtaining step, an angle maintaining or changing step, and a radial-coordinate maintaining or changing step. In the input step, an input processing unit performs an input process of a first color image signal. In the color information obtaining step, the color information obtaining section obtains two or more pieces of color information from the first color image signal. In the angle maintaining or changing step, an angle adjuster performs an equal angular magnification process and an angle expansion process or an angle compression process in a feature space formed by the two or more pieces of color information. The feature space includes first, second, and third areas to be observed. In the equal angular magnification process, an angle in a region R1x, which includes a first reference line passing through the second area, is maintained unchanged based on an angle change rate W1x. An angle in a region R1y located outside the region R1x is changed based on an angle change rate W1y greater than the angle change rate W1x in the angle expansion process or based on the angle change rate W1y less than the angle change rate W1x in the angle compression process. In the radial-coordinate maintaining or changing step, the radial-coordinate adjuster performs an equal radial-coordinate magnification process and a radial-coordinate expansion process or a radial-coordinate compression process. In the equal radial-coordinate magnification process, a radial coordinate in a region R2x, which includes a second reference line passing through the second area and intersecting the first reference line, is maintained unchanged based on a radial-coordinate change rate W2x. A radial coordinate in a region R2y located outside the region R2x is changed based on a radial-coordinate change rate W2y greater than the radial-coordinate change rate W2x in the radial-coordinate expansion process or based on a radial-coordinate change rate W2y less than the radial-coordinate change rate W2x in the radial-coordinate compression process.

According to the aspects of the present invention, an image that enables the distinction among the uninfection of *H. pylori*, the infection of the *H. pylori*, and the successful eradication of the *H. pylori* is produced.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

Figure 3:
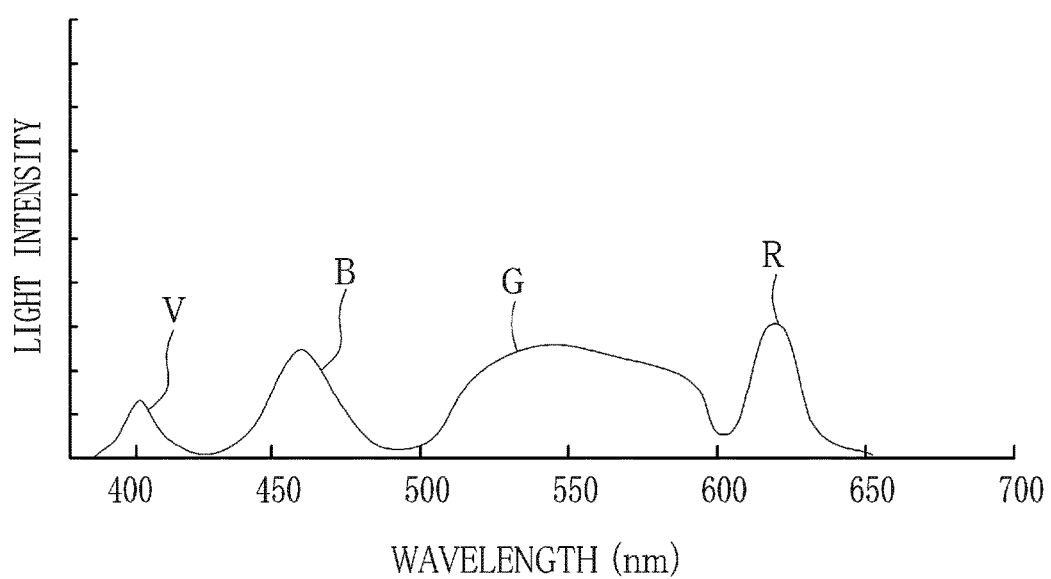
FIG. 3 is a graph illustrating emission spectra of violet light V, blue light B, green light G, and red light R.
Figure 8:
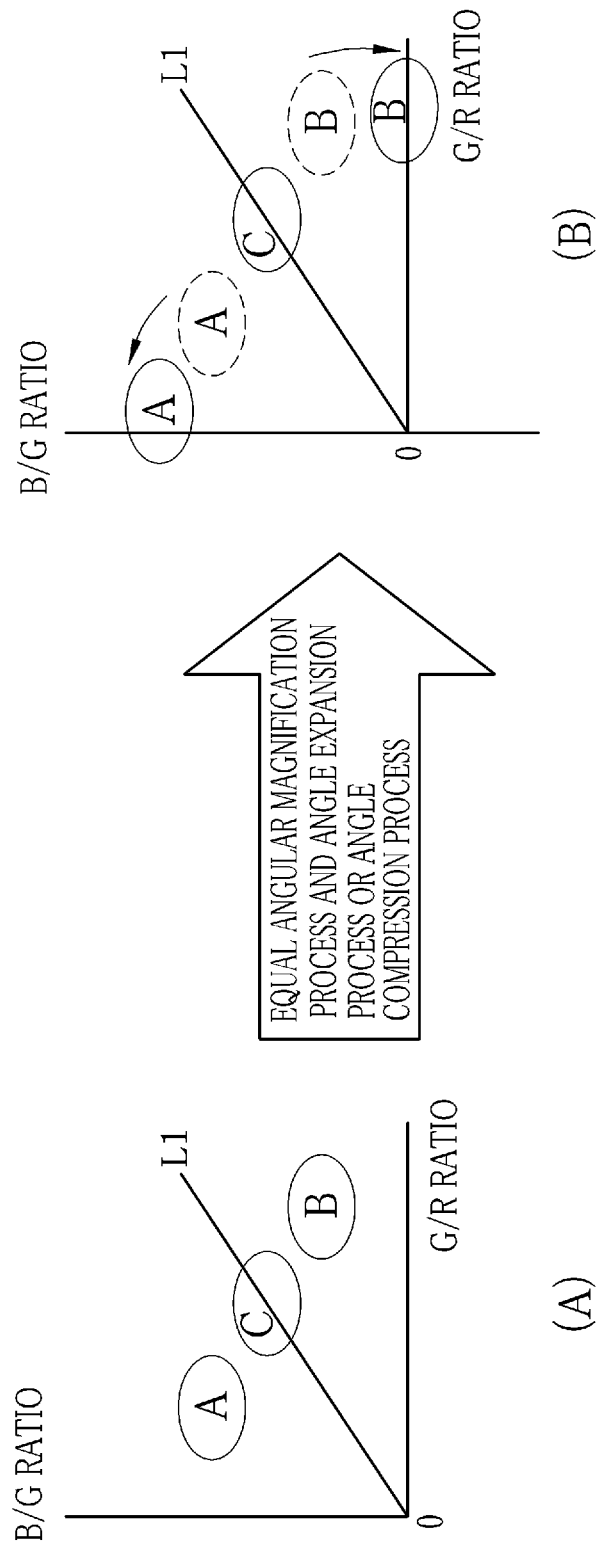
Figure 9:
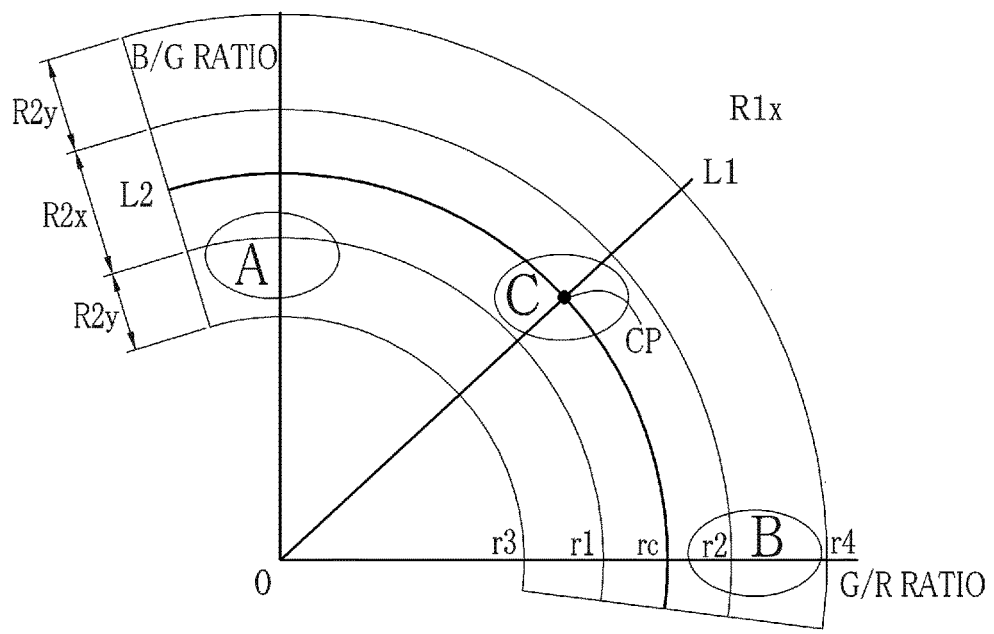
Figure 10:
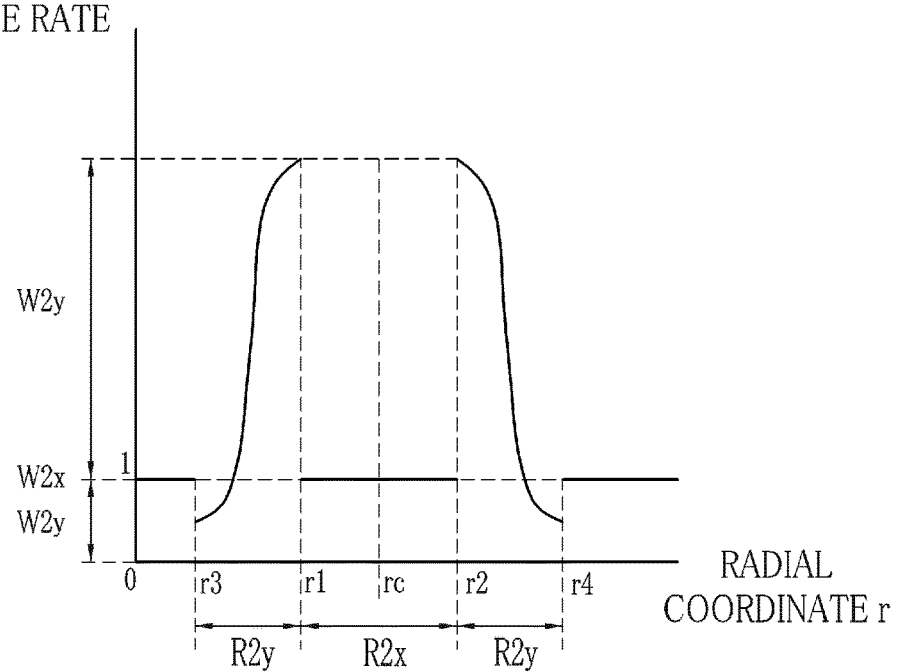
Figure 11:
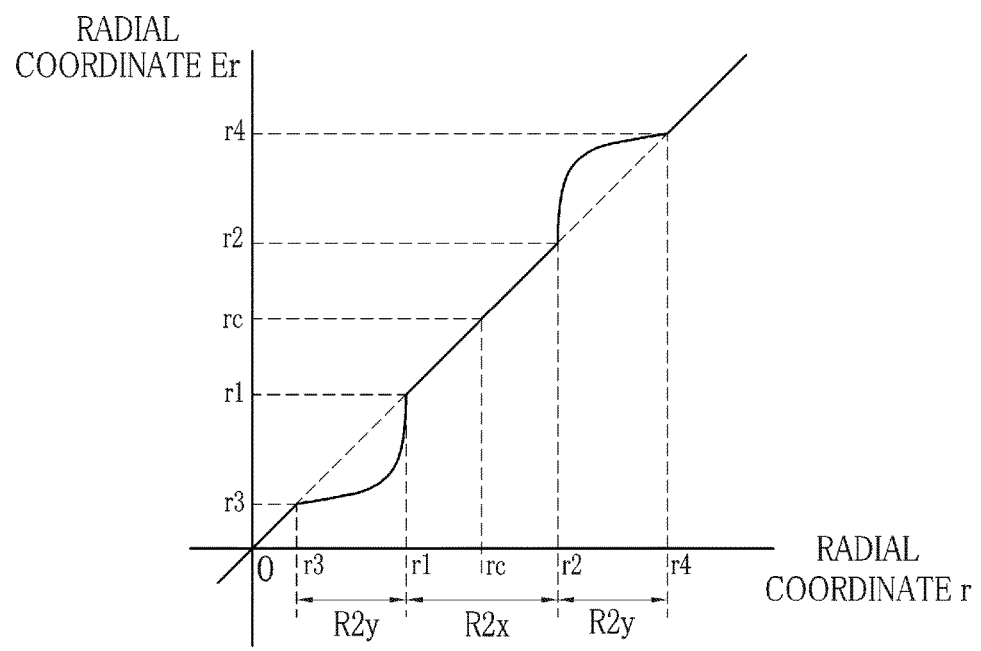
Figure 12:
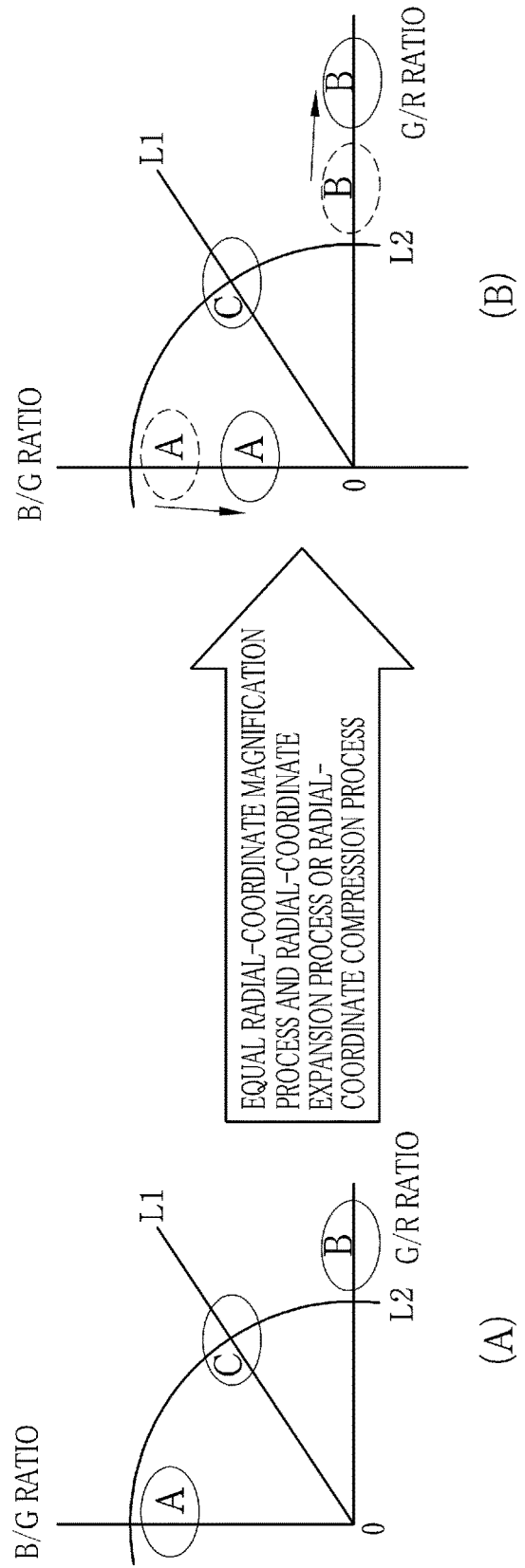
Figure 13:
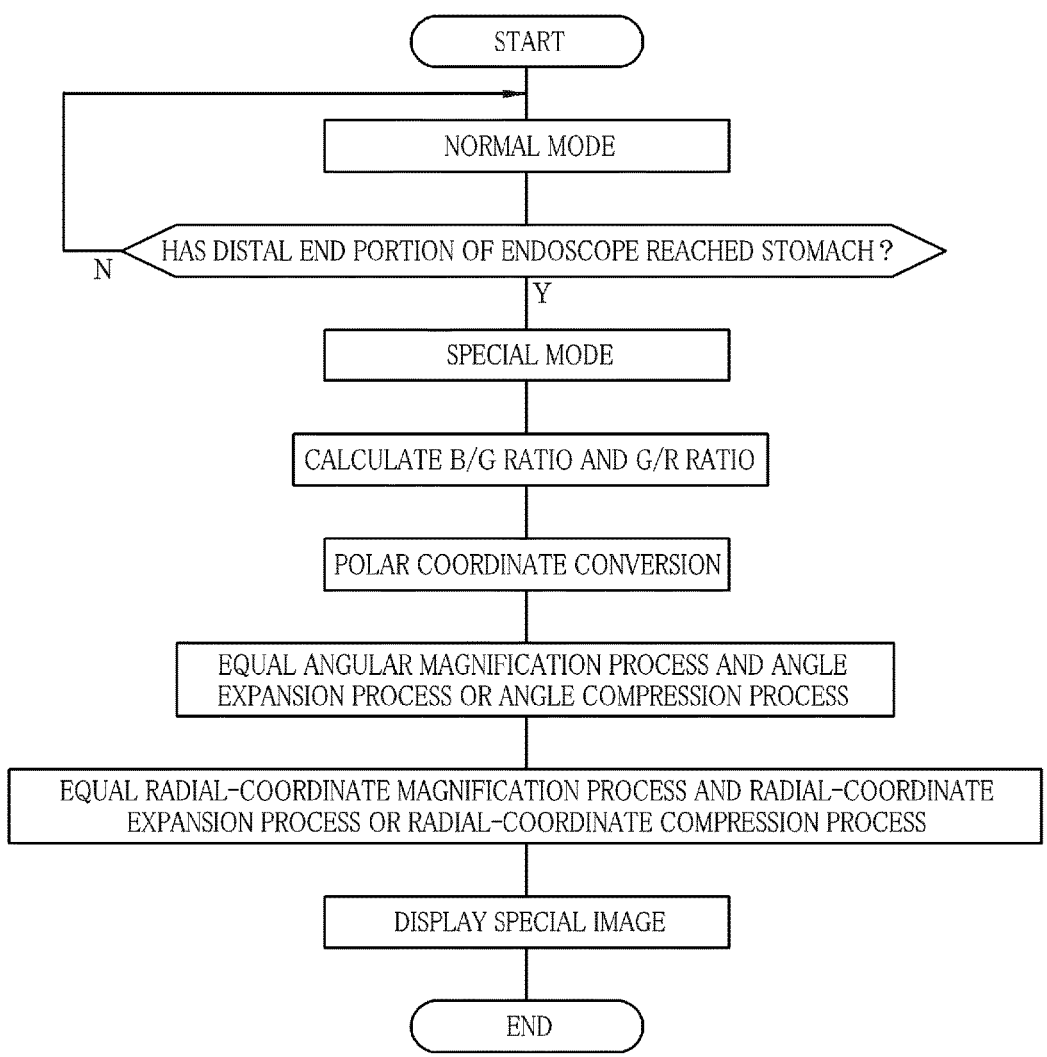
Figure 14:
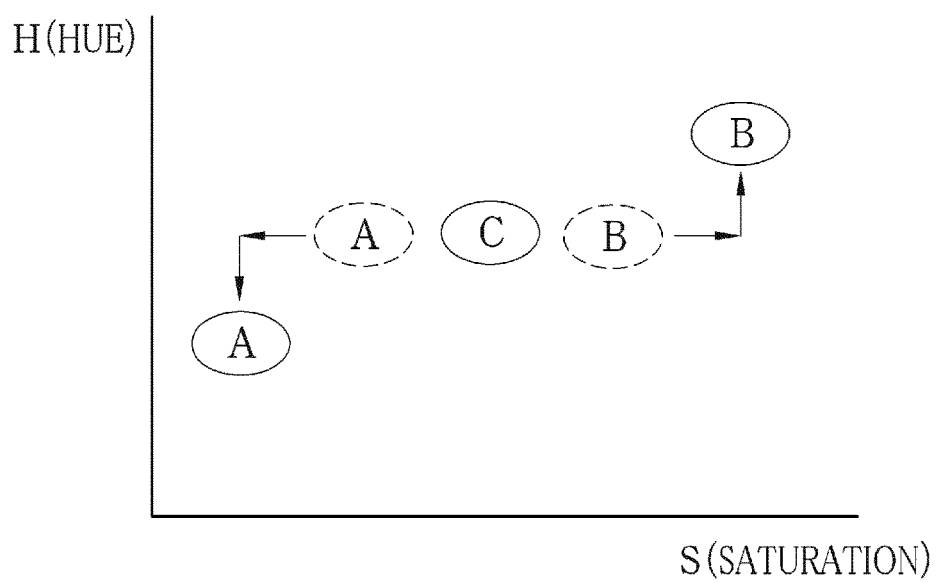
Figure 15:
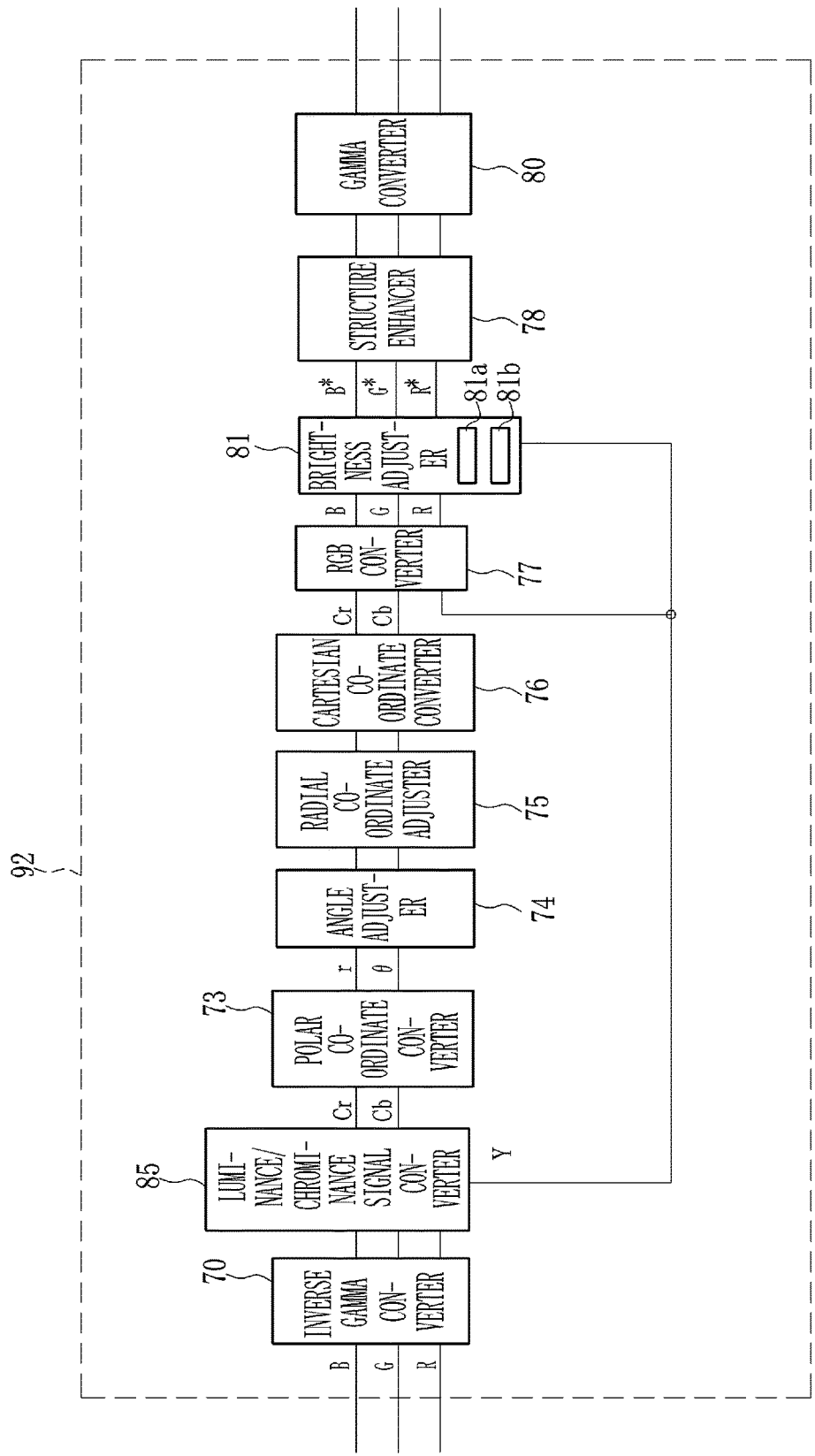
Figure 16:
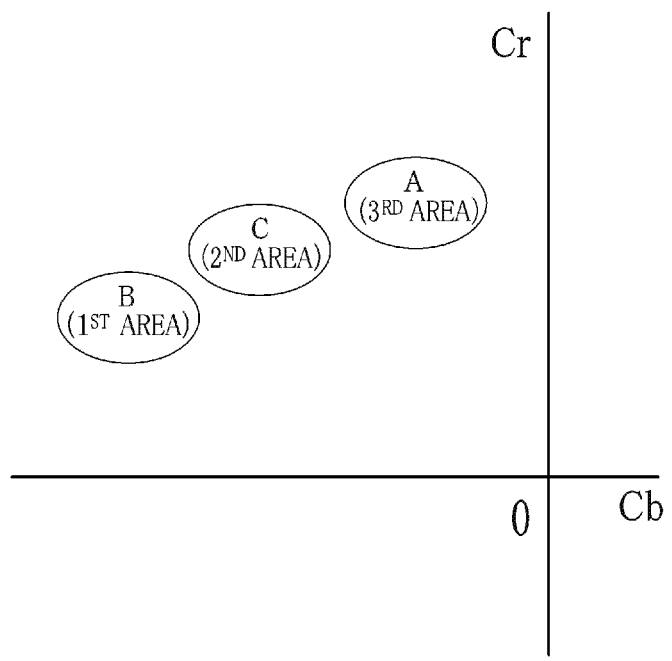
Figure 17:
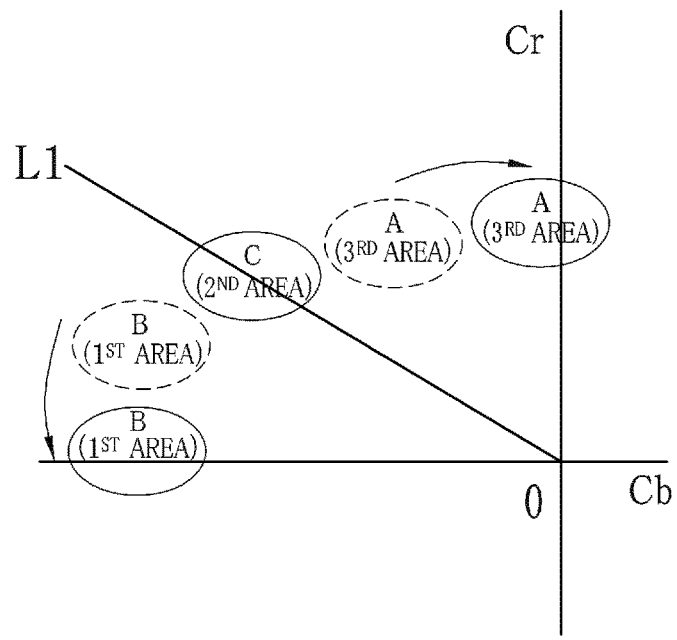
Figure 18:
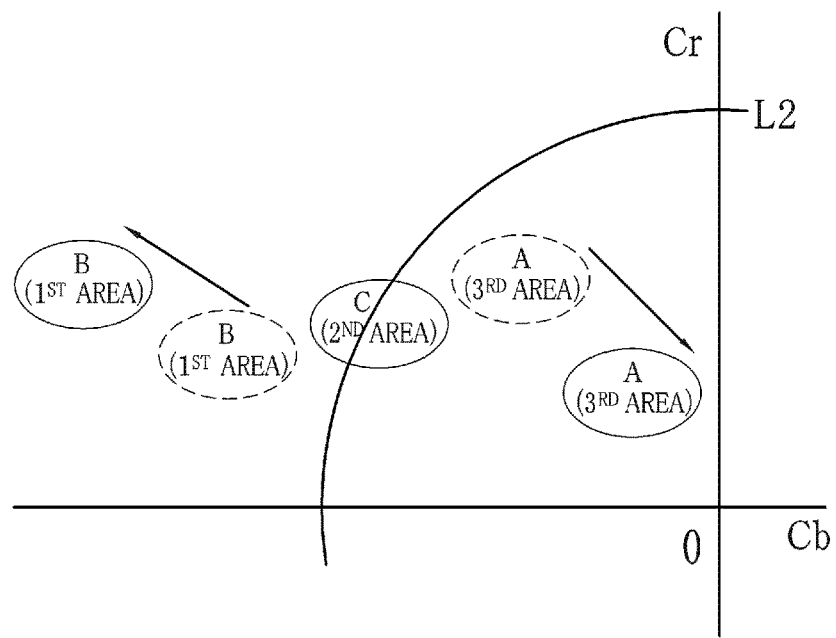
Figure 19:
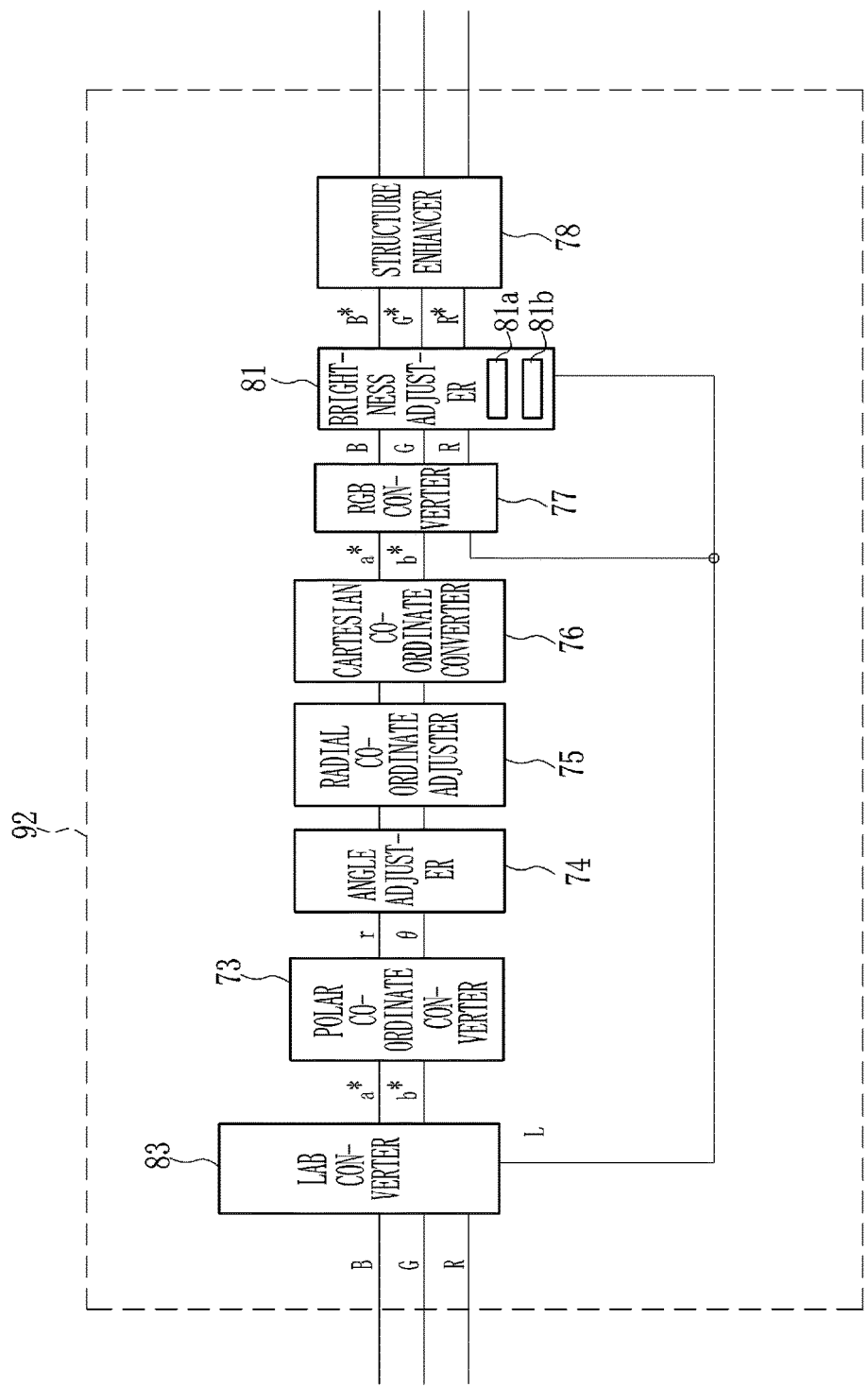
Figure 20:
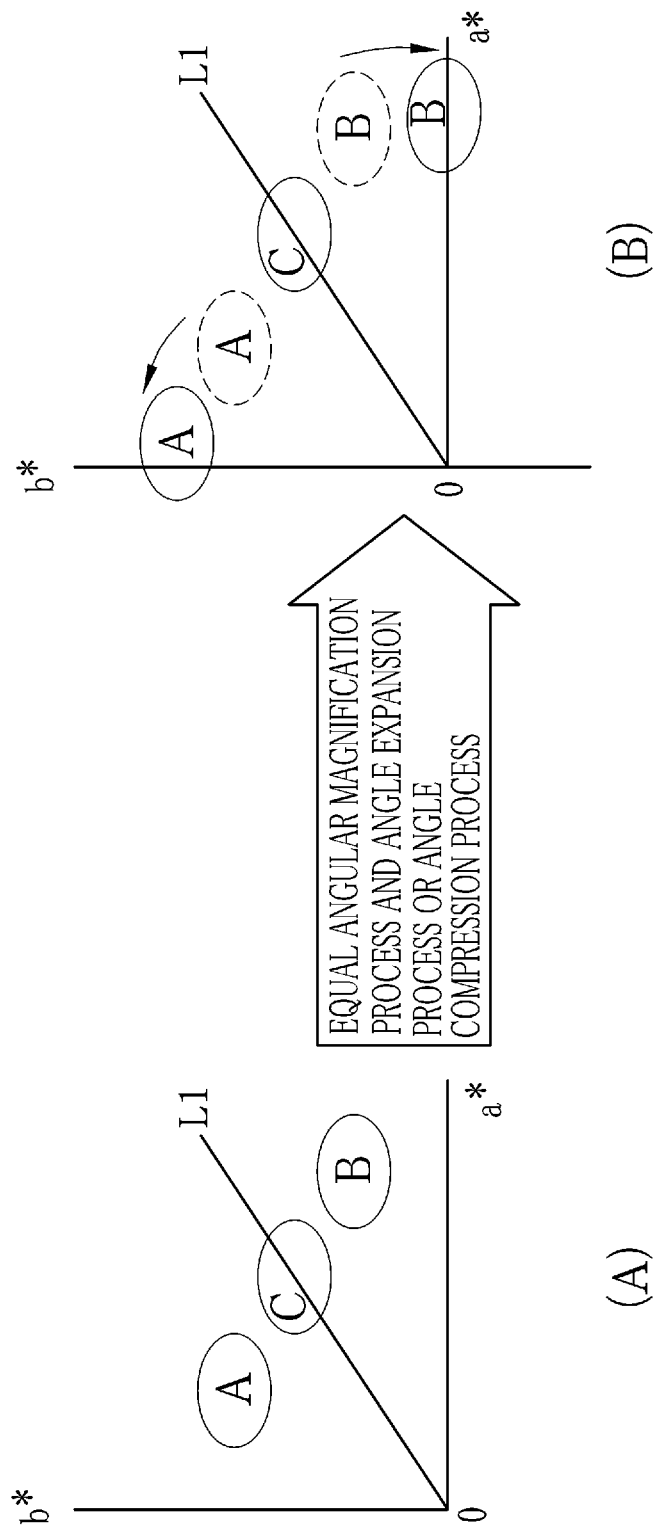
Figure 22:
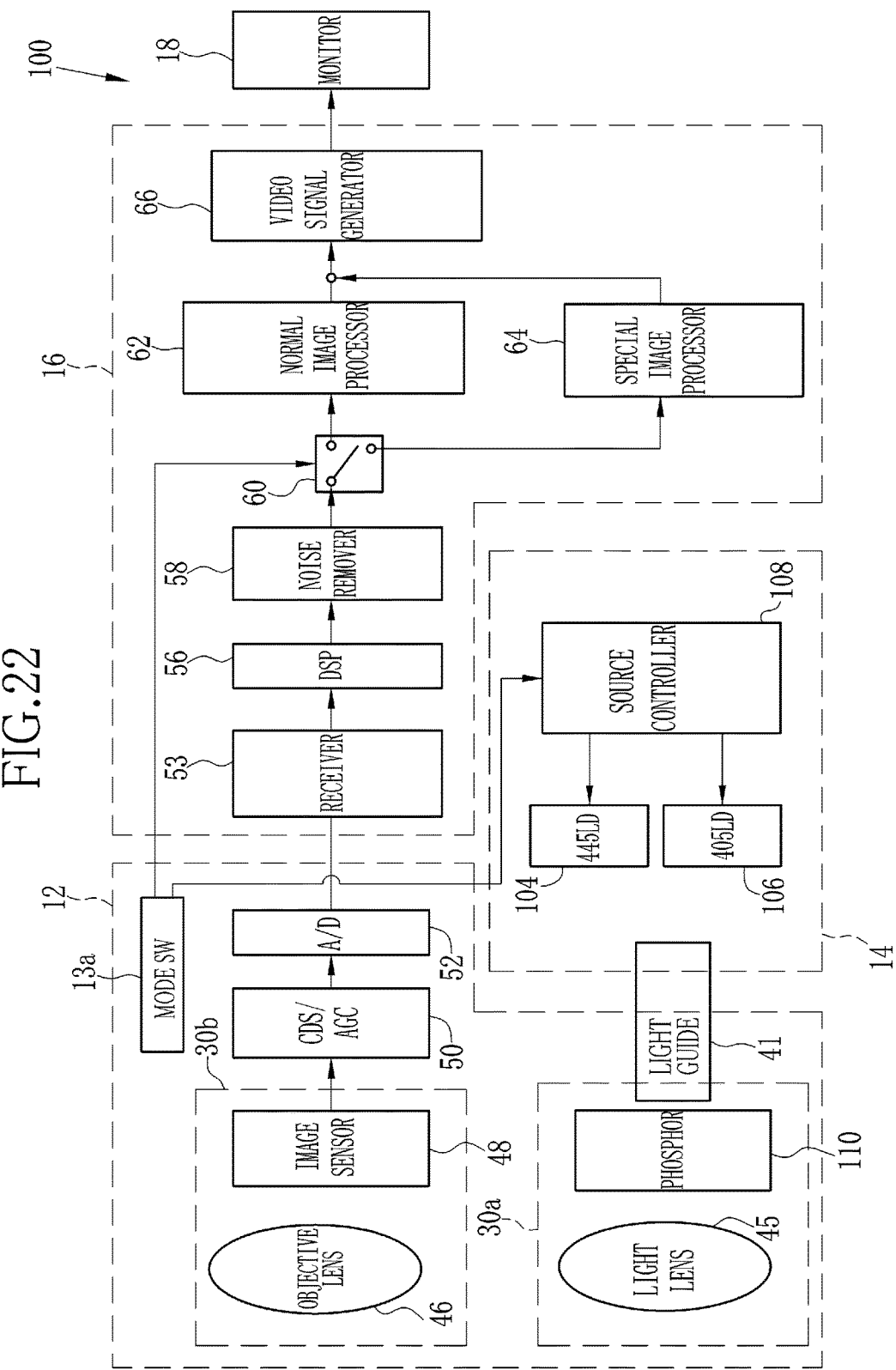
Figure 23:
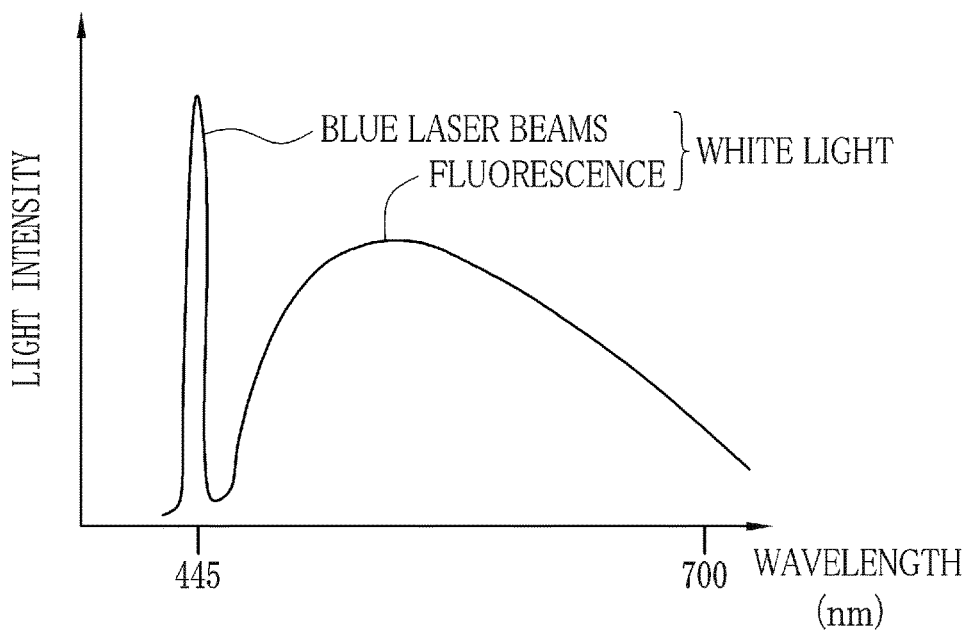
Figure 24:
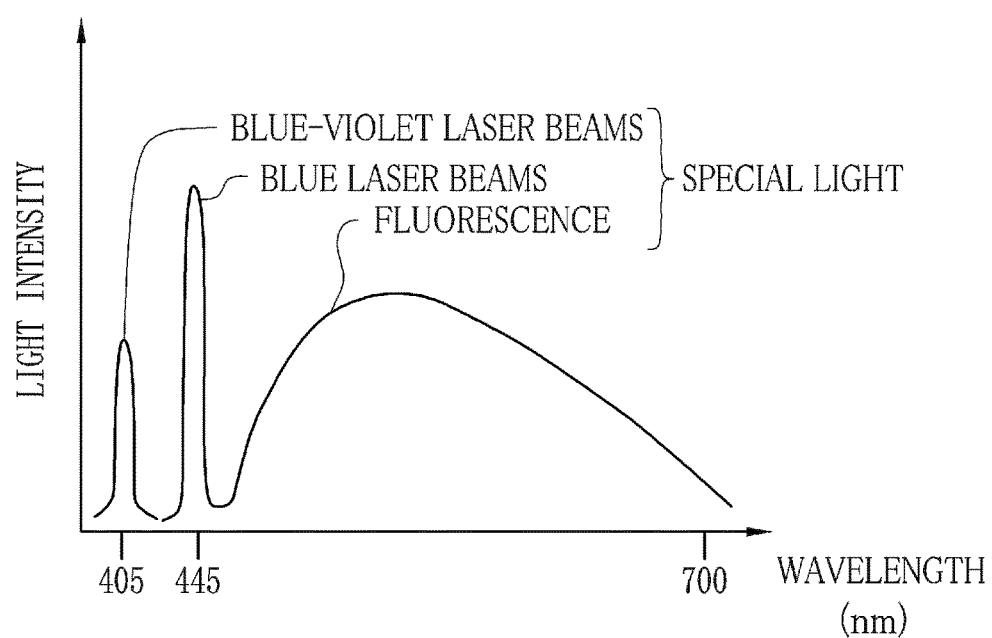
Figure 25:
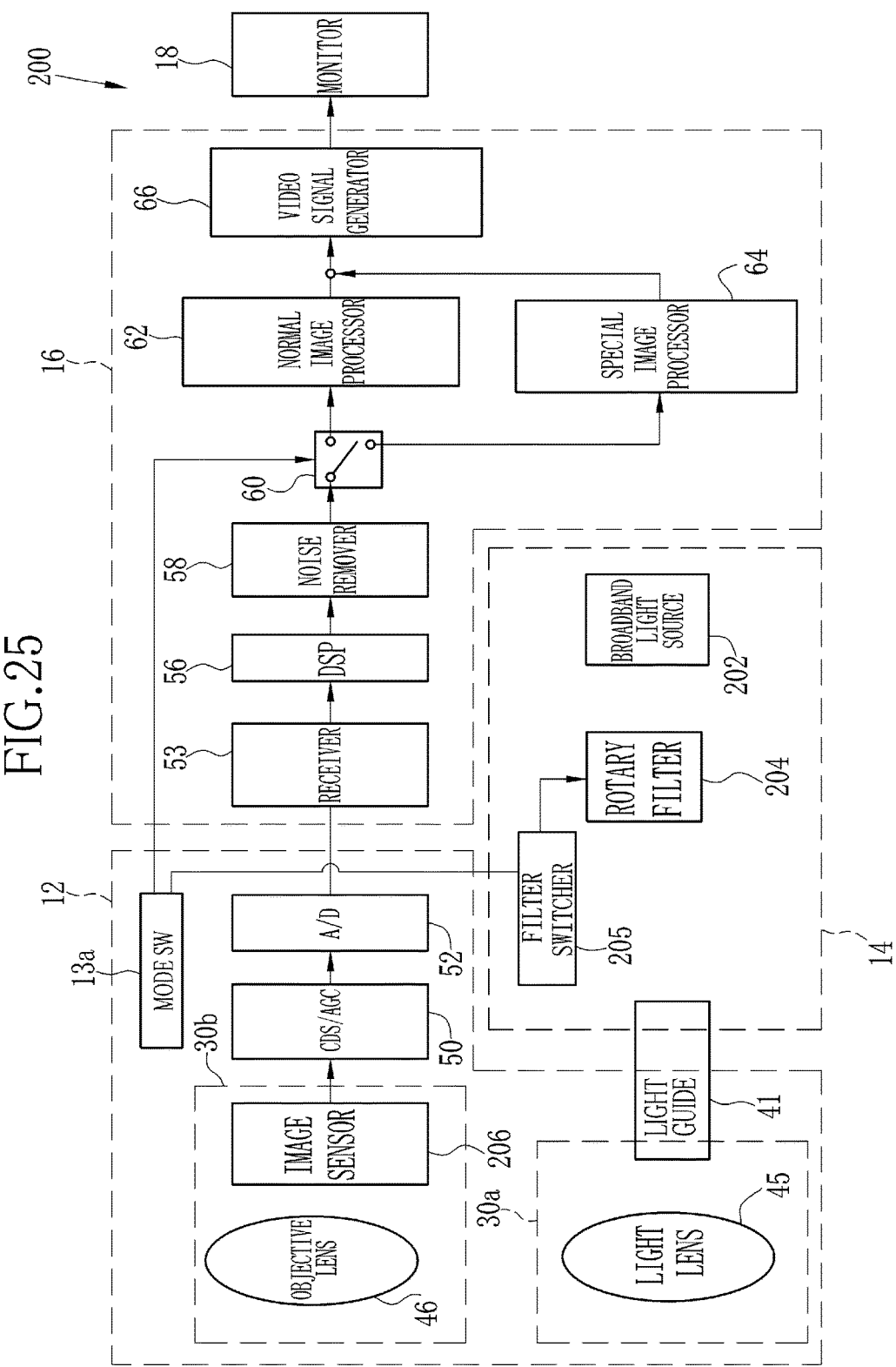
Figure 26:
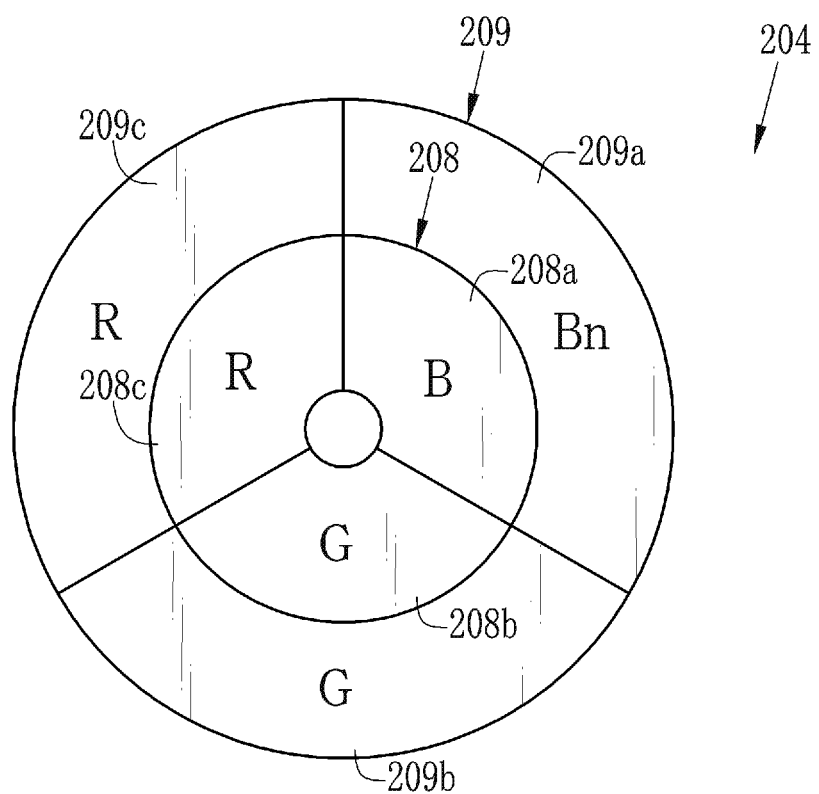
Figure 27:
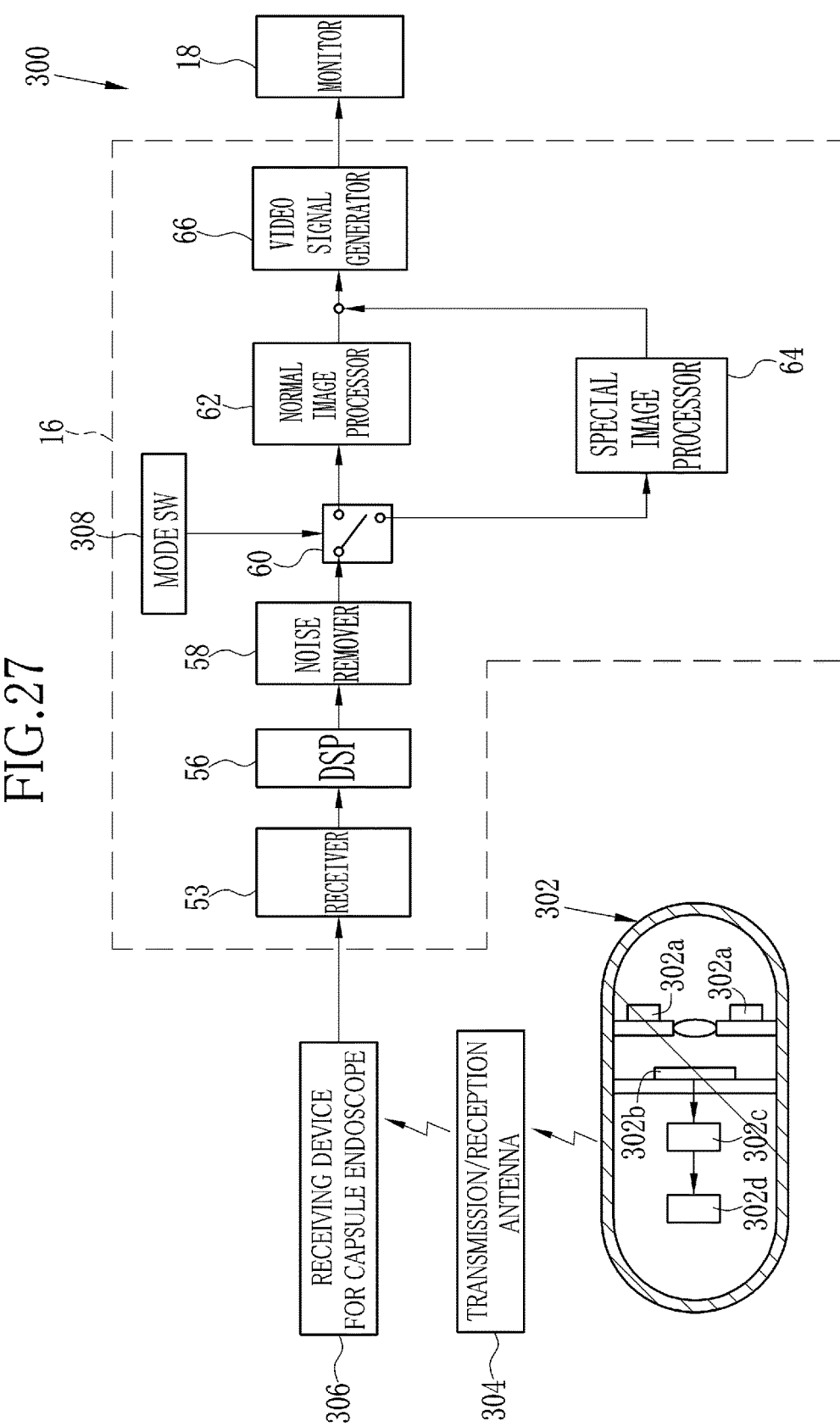
Figure 28:
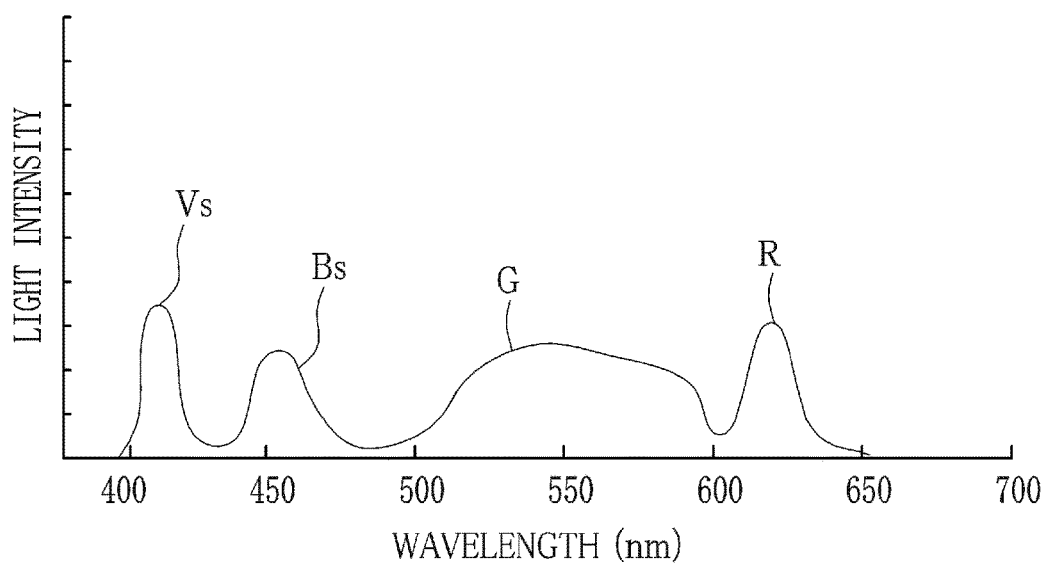
Figure 29:
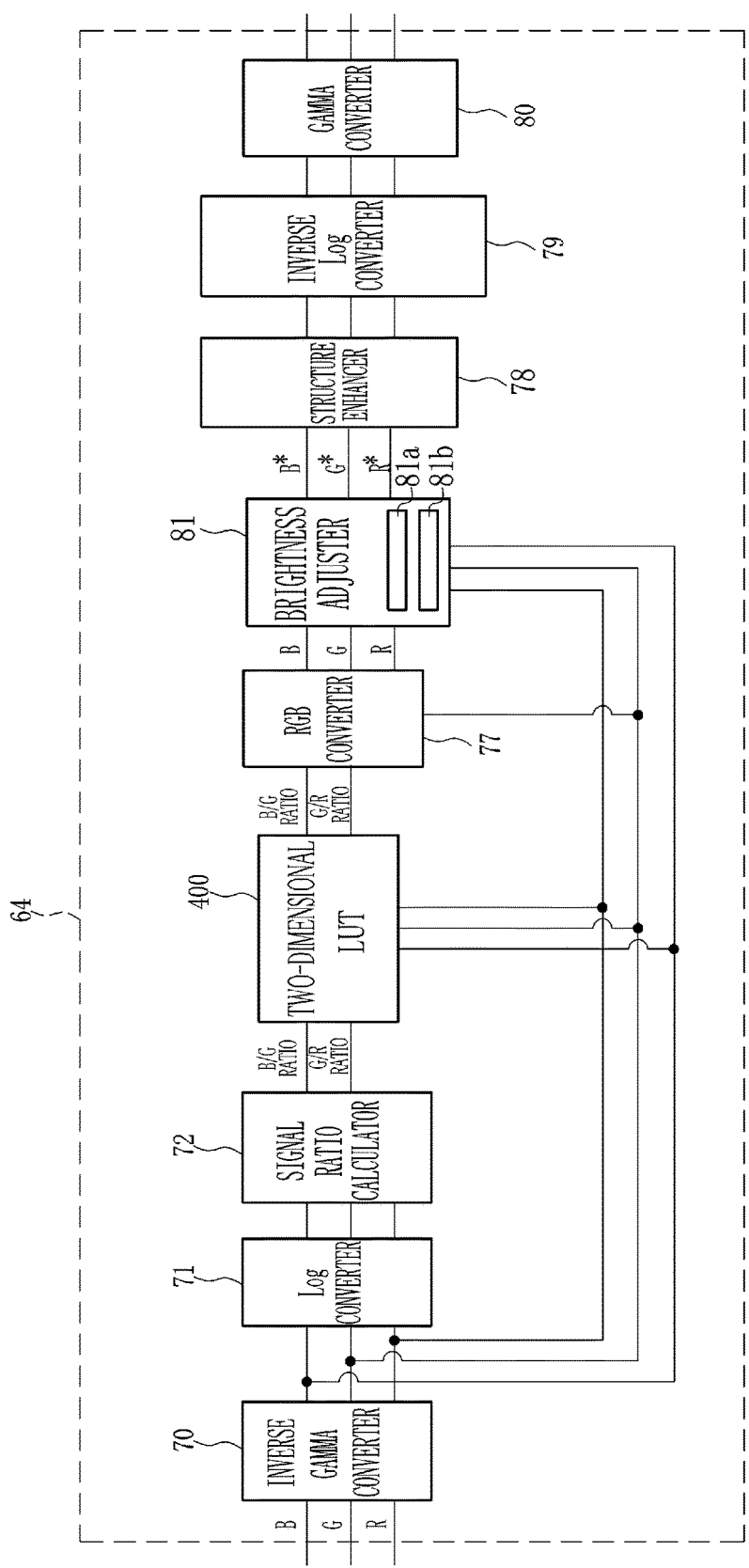
Figure 30:
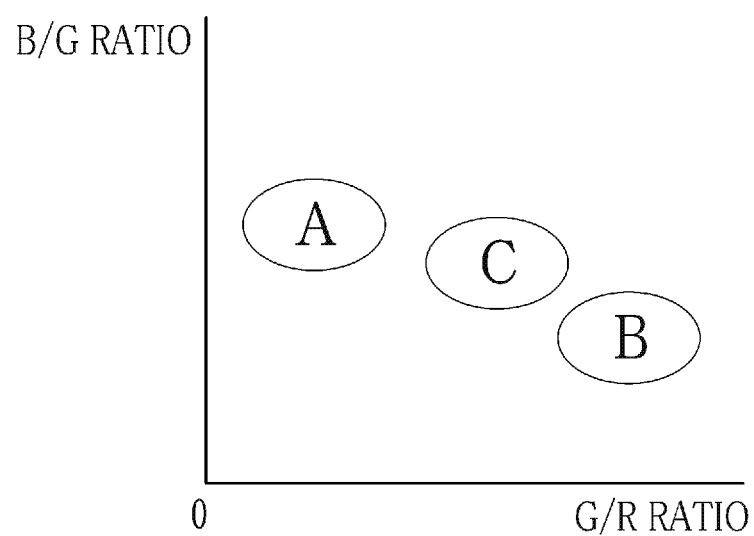

A part (A) of FIG. 8 is an explanatory view illustrating a state before an equal angular magnification process and an angle expansion process or an angle compression process (for the signal ratio space) and a part (B) of FIG. 8 is an explanatory view illustrating a state after the equal angular magnification process and the angle expansion process or the angle compression process (for the signal ratio space);

FIG. 9 is an explanatory view illustrating how to adjust a radial coordinate r;

FIG. 10 is a graph illustrating a relationship between radial coordinate r and radial-coordinate change rate;

FIG. 11 is a graph illustrating a relationship between radial coordinates r and Er;

A part (A) of FIG. 12 is an explanatory view illustrating a state before an equal radial-coordinate magnification process and a radial-coordinate expansion process or a radial-coordinate compression process (for the signal ratio space) and a part (B) of FIG. 12 is an explanatory view illustrating a state after the equal radial-coordinate magnification process and the radial-coordinate expansion process or the radial-coordinate compression process (for a signal ratio space);

FIG. 13 is a flowchart illustrating a procedure of observation of the object in a special mode;

FIG. 14 is an explanatory view illustrating distribution of first, second, and third areas before and after "the equal angular magnification process and the angle expansion process or the angle compression process" and "the equal radial-coordinate magnification process and the radial-coordinate expansion process or the radial-coordinate compression process" in HS space;

FIG. 15 is a block diagram illustrating functions of a special image processor in a case where the feature space is Cb-Cr space;

FIG. 16 is an explanatory view illustrating the distribution of the first area (B), the second area (C), and the third area (A) in the feature space (Cb-Cr space);

FIG. 17 is an explanatory view illustrating the distribution of the first, second, and third areas (B), (C), and (A) before and after the equal angular magnification process and the angle expansion process or the angle compression process for the Cb-Cr space;

FIG. 18 is an explanatory view illustrating the distribution of the first, second, and third areas (B), (C), and (A) before and after the equal radial-coordinate magnification process and the radial-coordinate expansion process or the radial-coordinate compression process for the Cb-Cr space;

FIG. 19 is a block diagram illustrating the functions of the special image processor in a case where the feature space is ab space;

A part (A) of FIG. 20 is an explanatory view illustrating a state before an equal angular magnification process and an angle expansion process or an angle compression process (for the ab space) and a part (B) of FIG. 20 is an explanatory view illustrating a state after the equal angular magnification process and the angle expansion process or the angle compression process (for the ab space);

A part (A) of FIG. 21 is an explanatory view illustrating a state before an equal radial-coordinate magnification process and a radial-coordinate expansion process or a radial-coordinate compression process (for the ab space) and a part (B) of FIG. 21 is an explanatory view illustrating a state after the equal radial-coordinate magnification process and the radial-coordinate expansion process or the radial-coordinate compression process (for the ab space);

FIG. 22 is a block diagram illustrating functions of an endoscope system according to an embodiment 2;

FIG. 23 is a graph illustrating an emission spectrum of white light;

FIG. 24 is a graph illustrating an emission spectrum of special light;

FIG. 25 is a block diagram illustrating functions of an endoscope system according to a third embodiment;

FIG. 26 is a plan view illustrating a rotary filter;

FIG. 27 illustrates functions of a capsule endoscope system according to an embodiment 4;

FIG. 28 is a graph illustrating emission spectra of violet light V, blue light B, green light G, and red light R that are different from those of FIG. 3;

FIG. 29 is a block diagram illustrating functions of the special image processor in a case where a two-dimensional LUT is used; and FIG. 30 is an explanatory view illustrating the distribution of an area (A), in which the coordinates corresponding to a portion uninfected with the *H. pylori* are distributed, an area (B), in which the coordinates corresponding to a portion infected with the *H. pylori* are distributed, and an area (C), in which the coordinates corresponding to a portion where the eradication of the *H. pylori* infection has been successful in a feature space (the vertical axis: B/G ratio, the horizontal axis: G/R ratio).

DESCRIPTION OF THE PREFERRED EMBODIMENTS

Embodiment 1A

Figure 1:
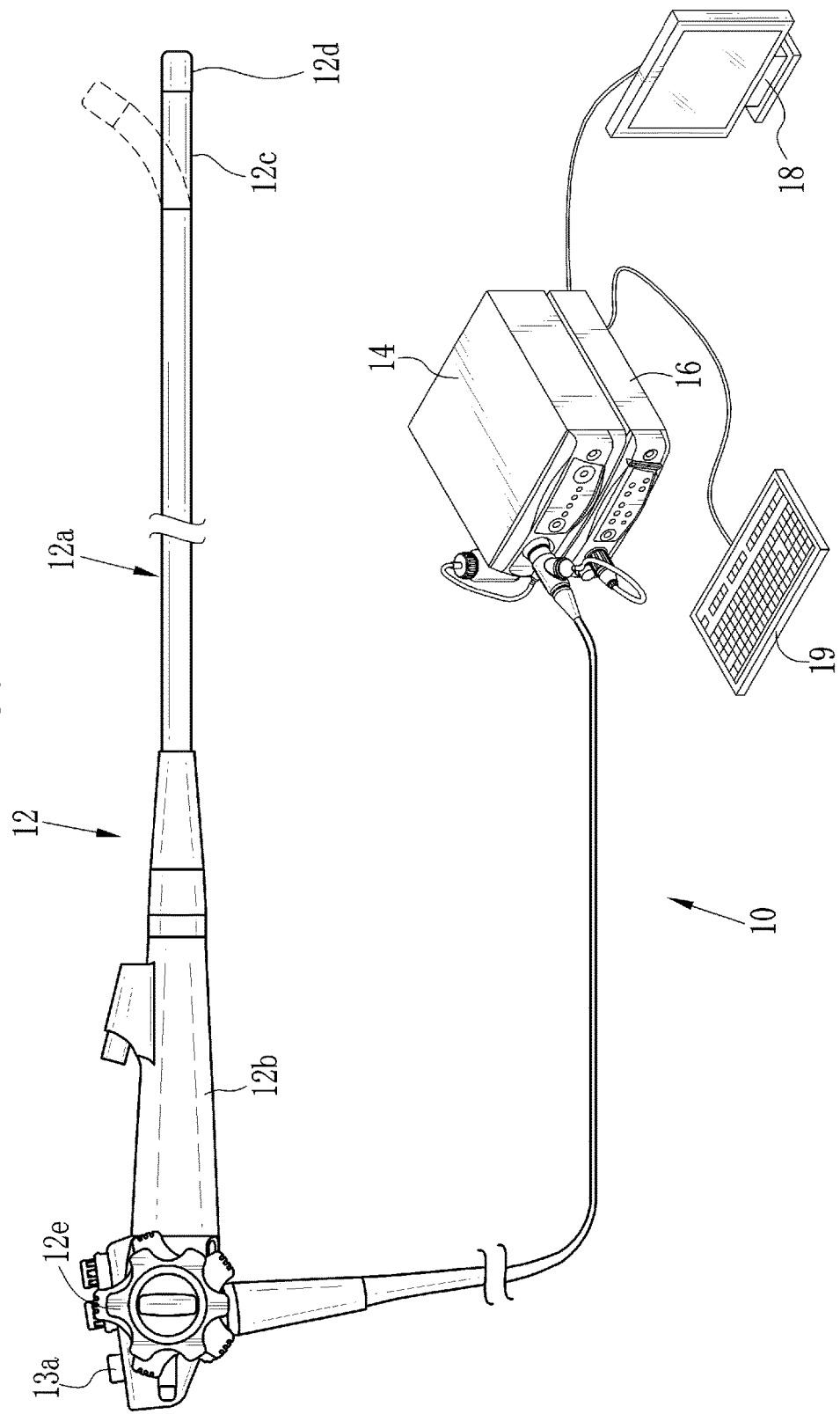
FIG. 1 is an external view of an endoscope of an embodiment 1A.

In FIG. 1, an endoscope system 10 according to an embodiment 1A comprises an endoscope 12, a light source device 14, a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, which is provided on the distal side of the insertion section 12a, and a distal end portion 12d coupled to the flexible portion 12c. The flexible portion 12c is bent by operating an angle knob 12e of the control handle unit 12b. Thereby the distal end portion 12d is directed to a desired direction.

The control handle unit 12b is provided with the angle knob 12e and a mode switch (SW) 13a. The mode SW 13a is operated to switch between a normal mode and a special mode. In the normal mode, a normal image is displayed on the monitor 18. The special mode is used to diagnose whether a patient is infected or not infected with *Helicobacter pylori* (*H. pylori*) or the eradication (removal) of the *H. pylori* infection has been successful. In the special mode, a special image is displayed on the monitor 18.

The processor device 16 is electrically connected to the monitor 18 and the console 19. The monitor 18 outputs and displays image information and the like. The console 19 functions as a UI (user interface), which receives an input operation such as setting a function. Note that an external storage unit (not shown) for recording the image information and the like may be connected to the processor device 16.

Figure 2:
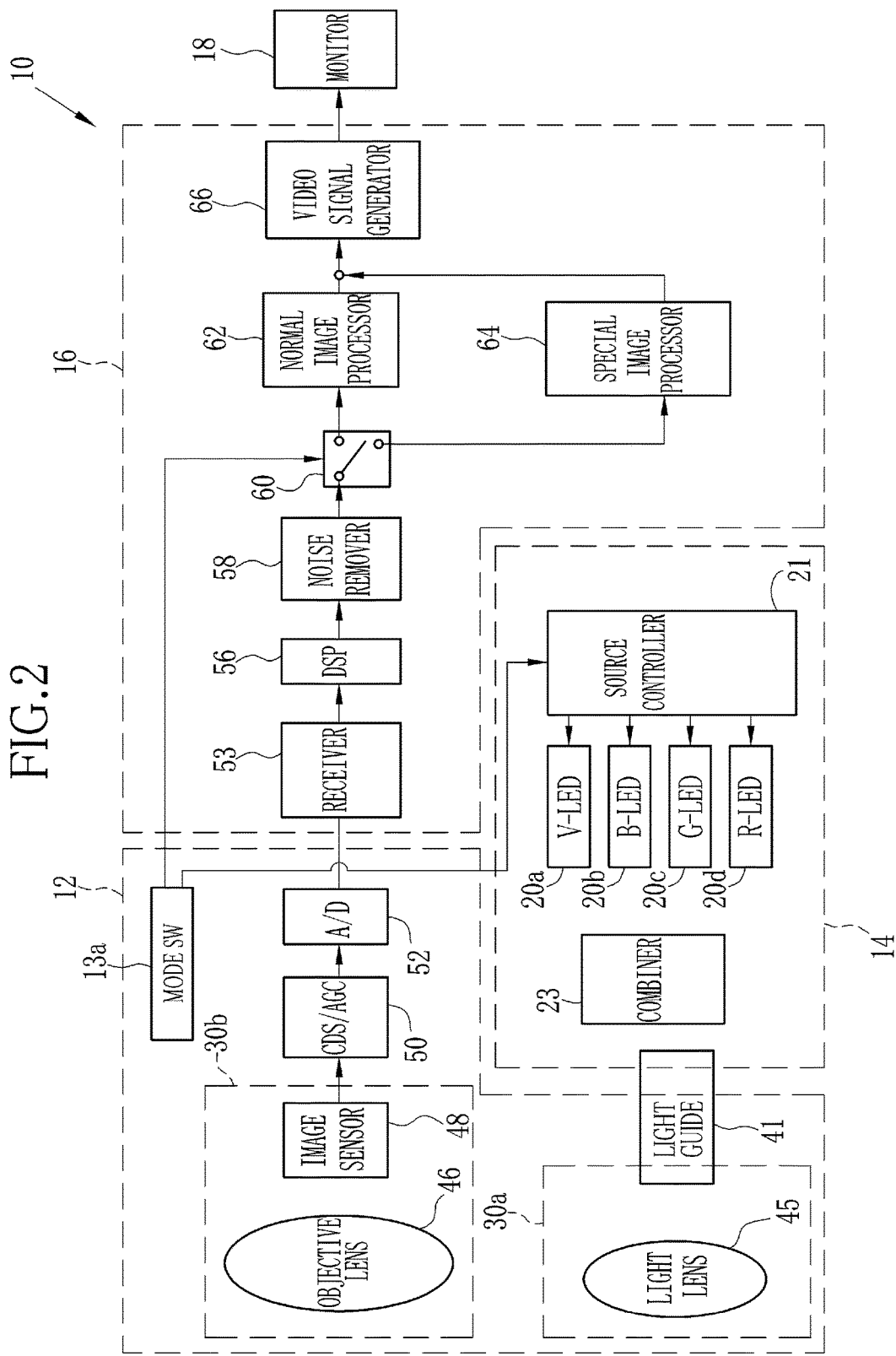
FIG. 2 is a block diagram illustrating functions of the endoscope of the embodiment 1A.

As illustrated in FIG. 2, the light source device 14 comprises a V-LED (Violet Light Emitting Diode) 20*a*, a B-LED (Blue Light Emitting Diode) 20*b*, a G-LED (Green Light Emitting Diode) 20*c*, an R-LED (Red Light Emitting Diode) 20*d*, a source controller 21 for controlling the LEDs 20*a* to 20*d*, and a combiner 23. The combiner 23 combines the optical paths of four colors of light from the four colors of LEDs 20*a* to 20*d* together. The light combined by the combiner 23 is applied to the object in a body cavity through a light guide (LG) 41 and a light lens 45. The light guide 41 extends inside the insertion section 12*a*. Note that an LD (Laser Diode) may be used in place of the LED.

As illustrated in FIG. 3, the V-LED 20*a* generates violet light V in a wavelength range of 380 to 420 nm and having the center wavelength 405±10 nm. The B-LED 20*b* generates blue light B in a wavelength range of 420 to 500 nm and having the center wavelength 460±10 nm. The G-LED 20*c* generates green light Gina wavelength range of 480 to 600 nm. The R-LED 20*d* generates red light R in a wavelength range of 600 to 650 nm and having the center wavelength in a range of 620 to 630 nm.

In each of the observation modes, the normal mode and the special mode, the source controller 21 turns on the V-LED 20*a*, the B-LED 20*b*, the G-LED 20*c*, and the R-LED 20*d*. In this case, the mixture of the violet light V, the blue light B, the green light G, and the red light R is applied to the object. The source controller 21 sets the light quantity ratios of the normal mode and the special mode different from each other. In the normal mode, the source controller 21 controls the LEDs 20*a* to 20*d* so that a light quantity ratio among the violet light V, the blue light B, the green light G, and the red light R is set to Vc:Bc:Gc:Rc. In the special mode, the source controller 21 controls the LEDs 20*a* to 20*d* so that the light quantity ratio among the violet light V, the blue light B, the green light G, and the red light R is set to Vs:Bs:Gs:Rs.

As illustrated in FIG. 2, the light guide 41 is incorporated in the endoscope 12 and a universal code that connects the endoscope 12, the light source device 14, and the processor device 16. The light guide 41 transmits the light combined by the combiner 23 to the distal end portion 12*d* of the endoscope 12. Note that a multimode fiber may be used as the light guide 41. For example, a small-diameter fiber cable with the core diameter 105 μm, the clad diameter 125 μm, and the outer diameter ϕ0.3 to 0.5 mm (including a protection layer, which is a jacket) may be used.

The distal end portion 12*d* of the endoscope 12 comprises an illumination optical system 30*a* and an imaging optical system 30*b*. The illumination optical system 30*a* has the light lens 45. The light from the light guide 41 is applied to the object through the light lens 45. The imaging optical system 30*b* has an objective lens 46 and an image sensor 48. The light reflected from the object is incident on the image sensor 48 through the objective lens 46. Thereby a reflection image of the object is formed on the image sensor 48.

The image sensor 48 is a color image sensor. The image sensor 48 captures the reflection image of the object, and outputs an image signal. It is preferred that the image sensor 48 is a CCD (Charge Coupled Device) image sensor, a CMOS (Complementary Metal-Oxide Semiconductor) image sensor, or the like. The image sensor 48 used in the embodiments of the present invention is a color image sensor that obtains image signals of three colors, R (red), G (green), and B (blue), that is, a so-called RGB image sensor comprising R pixels with R filters, G pixels with G filters, and B pixels with B filters.

Note that the image sensor 48 may be a so-called complementary color image sensor instead of the RGB image sensor. The complementary color image sensor has complementary color filters of C (cyan), M (magenta), Y (yellow), and G (green). In the case where the complementary color image sensor is used, four colors (CMYG) of image signals are outputted. It is necessary to convert the four colors (CMYG) of image signals into three colors (RGB) of image signals through complementary color/primary color conversion. Alternatively, the image sensor 48 may be a monochrome image sensor with no color filters. In this case, it is necessary that the source controller 21 allows emitting the blue light B, the green light G, and the red light R in a time-division manner. It is also necessary to add a synchronization process in processing the image signals.

The image signal outputted from the image sensor 48 is transmitted to a CDS/AGC circuit 50. The CDS/AGC circuit 50 performs correlated double sampling (CDS) and automatic gain control (AGC) on the image signal that is an analog signal. The image signal that has passed through the CDS/AGC circuit 50 is converted into a digital image signal by an A/D converter 52. The A/D converted digital image signal is inputted to the processor device 16.

The processor device 16 comprises a receiver 53, a DSP (Digital Signal Processor) 56, a noise remover 58, an image processing selector 60, a normal image processor 62, a special image processor 64, and a video signal generator 66. The receiver 53 receives the digital RGB image signals from the endoscope 12. The R image signal corresponds to the signals outputted from the R pixels of the image sensor 48. The G image signal corresponds to the signals outputted from the G pixels of the image sensor 48. The B image signal corresponds to the signals outputted from the B pixels of the image sensor 48.

The DSP 56 performs various types of signal processing such as defect correction process, offset processing, gain correction process, linear matrix processing, gamma conversion process, demosaicing process, and the like on the image signal received. In the defect correction process, signals from defective pixels in the image sensor 48 are corrected. In the offset processing, dark current components are removed from the RGB image signals which have been subjected to the defect correction process. Thereby an accurate zero level is set. In the gain correction process performed after the offset processing, a signal level is adjusted or corrected by multiplying the RGB image signals by a specific gain. After the gain correction process, the RGB image signals are subjected to the linear matrix processing to increase color reproducibility. Thereafter, brightness and saturation are adjusted or corrected through the gamma conversion process. After the linear matrix processing, the RGB image signals are subjected to the demosaicing process (also referred to as equalization process or synchronization process) in which color signal(s) lacking in each pixel is generated by interpolation. Owing to the demosaicing process, each pixel has three colors (RGB) of signals.

After the DSP 56 performs the gamma correction and the like on the RGB image signals, the noise remover 58 removes noise from the RGB image signals through a noise removing process (for example, a moving average method or a median filter method). The RGB image signals from which the noise has been removed are transmitted to the image processing selector 60. For example, an input processing unit of the present invention corresponds to the configuration comprising the receiver 53, the DSP 56, and the noise remover 58.

In the case of the normal mode set by operating the mode SW 13a, the image processing selector 60 transmits the RGB image signals to the normal image processor 62. In the case of the special mode, the image processing selector 60 transmits the RGB image signals to the special image processor 64.

The normal image processor 62 performs a color conversion process, a color enhancement process, and a structure enhancement process on the RGB image signals. In the color conversion process, the digital RGB image signals are subjected to 3×3 matrix processing, tone conversion process, three-dimensional LUT process, or the like. Thereby the digital RGB image signals are converted into color-converted RGB image signals. Next, the color-converted RGB image signals are subjected to various types of color enhancement processes. Thereby the color-converted RGB image signals are converted into color-enhanced RGB image signals. The color-enhanced RGB image signals are subjected to the structure enhancement process (e.g. spatial frequency enhancement and the like). Thereby the color-enhanced RGB image signals are converted into structure-enhanced RGB image signals. The structure-enhanced RGB image signals are inputted as the RGB image signals of the normal image from the normal image processor 62 to the video signal generator 66.

The special image processor 64 produces the special image based on the RGB image signals. In the special image, differences in color of the object among a portion uninfected (not yet infected) with the *H. pylori*, a portion infected with the *H. pylori*, a portion in which the *H. pylori* infection has been eradicated successfully are enhanced. The special image processor 64 will be described in detail below. The RGB image signals of the special image, which is produced by the special image processor 64, are inputted to the video signal generator 66.

The video signal generator 66 converts the RGB image signals, which are inputted from the normal image processor 62 or the special image processor 64, into a video signal to be displayed as an image on the monitor 18. Based on the video signal, the monitor 18 displays the normal image and/or the special image.

Figure 4:
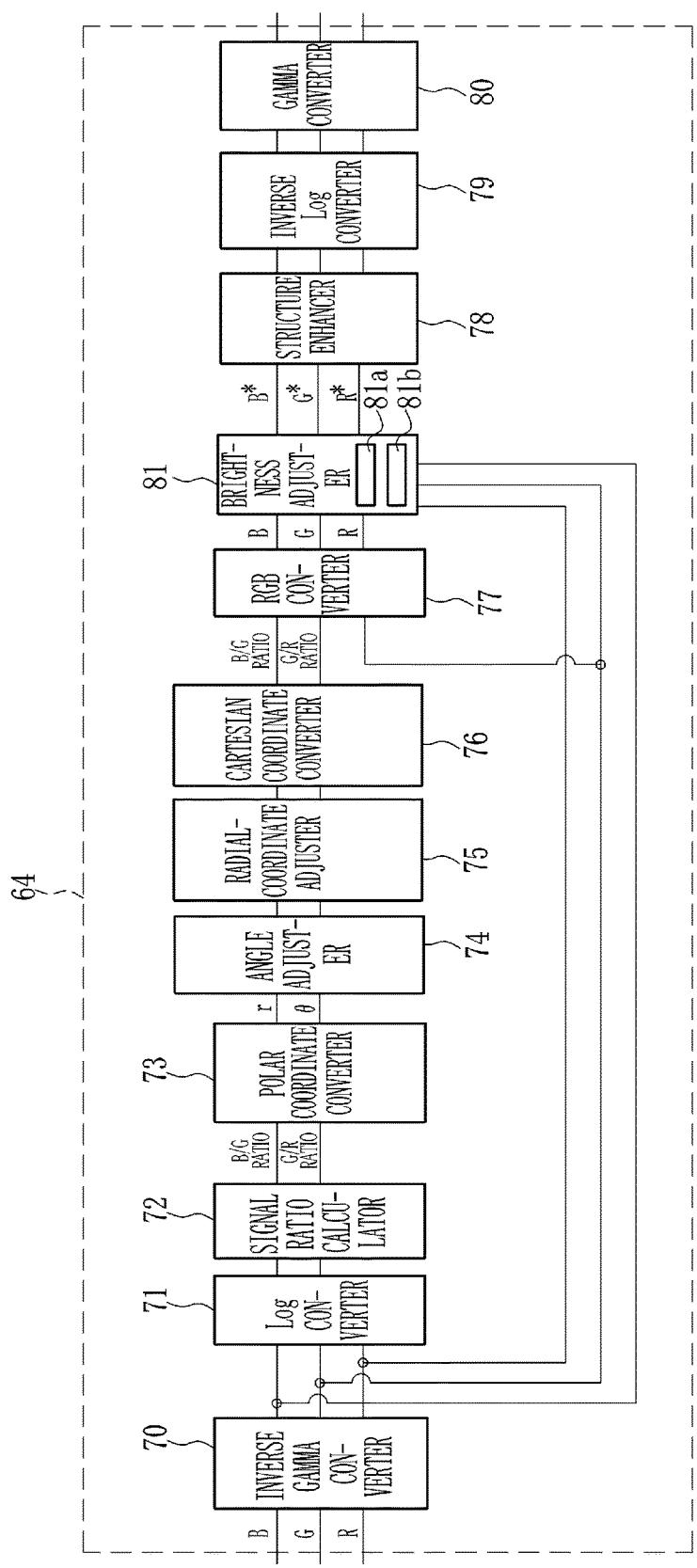
FIG. 4 is a block diagram illustrating functions of a special image processor in a case where the feature space is a signal ratio space.

As illustrated in FIG. 4, the special image processor 64 comprises an inverse gamma converter 70, a log converter 71, a signal ratio calculator 72, a polar coordinate converter 73, an angle adjuster 74, a radial-coordinate adjuster 75, a Cartesian coordinate converter 76, an RGB converter 77, a structure enhancer 78, an inverse log converter 79, and a gamma converter 80. The special image processor 64 also comprises a brightness adjuster 81 between the RGB converter 77 and the structure enhancer 78.

The inverse gamma converter 70 performs inverse gamma conversion on the inputted digital image signals of the RGB channels. The RGB image signals after the inverse gamma conversion are linearly-changing RGB signals, which change linearly relative to reflectance from the object. Owing to this, a proportion of the signal components related to various types of biological information of the object increases in the RGB image signals. Note that the linearly-changing R image signal is referred to as a first R image signal. The linearly-changing G image signal is referred to as a first G image signal. The linearly-changing B image signal is referred to as a first B image signal.

The log converter 71 performs log conversion of each of the linearly-changing RGB image signals (which correspond to a first color image signal of the present invention, for example). Thereby, log-converted R image signal (log R), log-converted G image signal (log G), and log-converted B image signal (log B) are obtained. The signal ratio calculator 72 (which corresponds to a color information obtaining section of the present invention, for example) performs difference processing (log G−log B=log G/B=−log(B/G)) based on the log-converted G image signal and the log-converted B image signal. Thereby, the B/G ratio is calculated. The B/G ratio refers to −log(B/G) with "−log" omitted. The G/R ratio is calculated by difference processing (log R−log G=log R/G=−log(G/R)) based on the log-converted R image signal and the log-converted G image signal. The G/R ratio refers to −log(G/R) with "−log" omitted in a manner similar to the B/G ratio.

Note that the B/G ratio and the G/R ratio are calculated from the pixel values of the pixels located in the same (or corresponding) positions in the B image signal, the G image signal, and the R image signal. The B/G ratio and the G/R ratio are calculated for each pixel. The B/G ratio correlates with a blood vessel depth (distance between the mucosal surface and a position of a specific blood vessel), so that the B/G ratio varies with the blood vessel depth. The G/R ratio correlates with the blood volume (hemoglobin index), so that the G/R ratio varies with the blood volume.

The polar coordinate converter 73 converts the B/G ratio and the G/R ratio, which are calculated by the signal ratio calculator 72, into a radial coordinate r and an angle θ. The polar coordinate converter 73 performs the conversion into the radial coordinate r and the angle θ for each pixel. The angle adjuster 74 performs a process for adjusting the angles θ in the first, second, and third areas in the signal ratio space formed by the B/G ratio and the G/R ratio and thereby increases the difference (or a distance) between the first and second areas and the difference (or a distance) between the second and third areas. In the first area, the radial coordinates r and the angles θ corresponding to a portion (of the object) infected with the *H. pylori* are distributed. In the second area, the radial coordinates r and the angles θ corresponding to a portion (of the object) in which the eradication of the *H. pylori* infection has been successful are distributed. In the third area, the radial coordinates r and the angles θ corresponding to a portion (of the object) uninfected (not yet infected) with the *H. pylori* are distributed. The process for adjusting the angle θ, which is performed by the angle adjuster 74, will be described below. The radial-coordinate adjuster 75 performs a process for adjusting the radial coordinates r in the first, second, and third areas and thereby increases the difference (or a distance) between the first and second areas and the difference (or a distance) between the second and third areas. The process for adjusting the radial coordinate r, which is performed by the radial-coordinate adjuster 75, will be described below.

The Cartesian coordinate converter 76 converts the radial coordinate r and the angle θ, which have passed through the angle adjuster 74 and the radial-coordinate adjuster 75, into Cartesian coordinates. Thereby the radial coordinate r and the angle θ are converted into the B/G and G/R ratios whose angle θ and radial coordinate r have been adjusted. The RGB converter 77 (which corresponds to a color image signal converter of the present invention, for example) uses at least one of the first RGB image signals to convert the B/G and G/R ratios whose angle θ and radial coordinate r have been adjusted, into second RGB image signals. To convert the B/G ratio into the second B image signal, the RGB converter 77 performs arithmetic operations based on the B/G ratio whose angle θ and radial coordinate r have been adjusted and the first G image signal of the first RGB image signals, for example. To convert the G/R ratio into the second R image signal, the RGB converter 77 performs arithmetic operations based on the G/R ratio whose angle θ and radial coordinate r have been adjusted and the first G image signal of the first RGB image signals, for example. The RGB converter 77 outputs the first G image signal as the second G image signal, without any conversion.

The brightness adjuster 81 adjusts or corrects the pixel values of the second RGB image signals based on the first RGB image signals and the second RGB image signals. A reason for adjusting the pixel values of the second RGB image signals by the brightness adjuster 81 is as follows. The brightness of the second RGB image signals, which have been subjected to the process for changing color regions (color areas) performed by the angle adjuster 74 and the radial-coordinate adjuster 75, may become significantly different from the brightness of the first RGB image signals. The brightness adjuster 81 adjusts the pixel values of the second RGB image signals to make the brightness of the second RGB image signals after the brightness adjustment equal to the brightness of the first RGB image signals.

The brightness adjuster 81 comprises a first brightness information calculator 81a and a second brightness information calculator 81b. The first brightness information calculator 81a calculates first brightness information Yin based on the first RGB image signals. The second brightness information calculator 81b calculates second brightness information Yout based on the second RGB image signals. The first brightness information calculator 81a calculates the first brightness information Yin with the use of an arithmetic expression "kr×pixel value of first R image signal+kg×pixel value of first G image signal+kb×pixel value of first B image signal". The second brightness information calculator 81b calculates the second brightness information Yout in a manner similar to that of the first brightness information calculator 81a, with the use of an arithmetic expression similar to that described above. After calculating the first brightness information Yin and the second brightness information Yout, the brightness adjuster 81 performs arithmetic operations based on the expressions (E1) to (E3), thereby adjusting the pixel values of the second RGB image signals.

$$R^* = \text{pixel value of second } R \text{ image signal} \times Yin/Yout \quad (E1)$$

$$G^* = \text{pixel value of second } G \text{ image signal} \times Yin/Yout \quad (E2)$$

$$B^* = \text{pixel value of second } B \text{ image signal} \times Yin/Yout \quad (E3)$$

Note that "R*" denotes the second R image signal after the brightness adjustment. "G*" denotes the second G image signal after the brightness adjustment. "B*" denotes the second B image signal after the brightness adjustment. Each of "kr", "kg", and "kb" is any constant within a range from 0 to 1.

The structure enhancer 78 performs the structure enhancement process on the second RGB image signals which have passed through the brightness adjuster 81. Frequency filtering or the like may be used for the structure enhancement process. The inverse log converter 79 performs inverse log conversion on the second RGB image signals which have passed through the structure enhancer 78. Thereby the second RGB image signals with antilogarithmic pixel values are obtained. The gamma converter 80 performs the gamma conversion on the RGB image signals which have passed through the inverse log converter 79. Thereby the second RGB image signals with the tone suitable for an output device such as the monitor 18 are obtained. The RGB image signals, which have passed through the gamma converter 80, are transmitted as the RGB image signals of the special image to the video signal generator 66.

Figure 5:
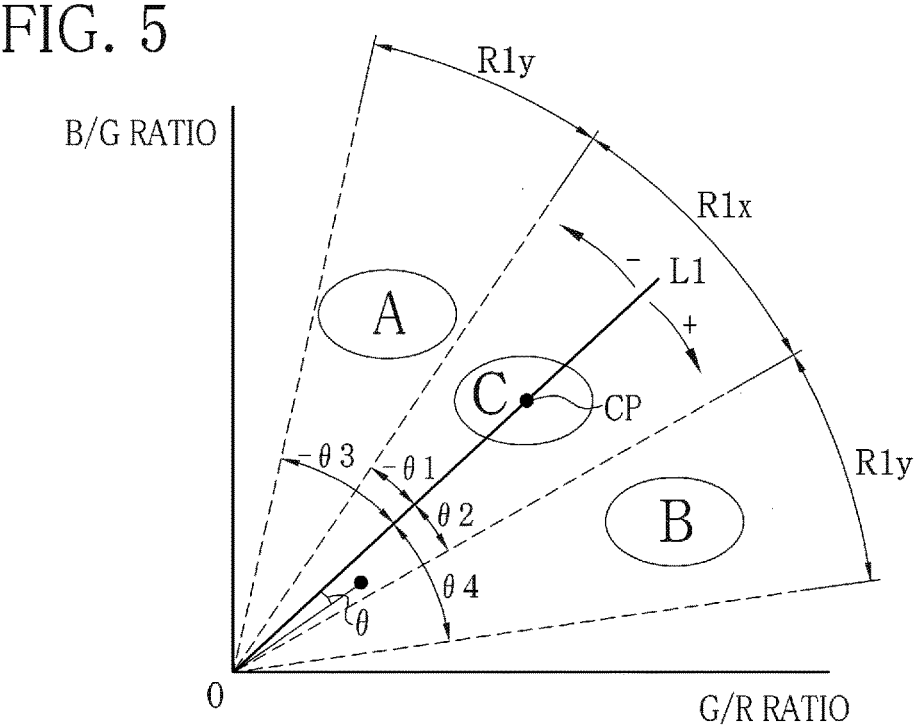
FIG. 5 is an explanatory view illustrating how to adjust an angle θ.

Hereinafter, a process for adjusting an angle θ, which is performed by the angle adjuster 74, is described. As illustrated in FIG. 5, in the signal ratio space, that is, the feature space formed by the B/G ratio and the G/R ratio, all of the first area (denoted as "B"), the second area (denoted as "C"), and the third area (denoted as "A"), which are included in the object, are distributed in the first quadrant. A first reference line L1 passes through a barycentric position CP of the second area (C). The first area (B) is located on the positive side of the horizontal axis (the G/R ratio) with respect to the first reference line L1. The third area (A) is located on the negative side of the horizontal axis (the G/R ratio) with respect to the first reference line L1, that is, opposite to the first area (B) with respect to the first reference line L1. Note that the barycentric position CP of the second area (C) is calculated based on the B/G ratio and the G/R ratio in the second area. The first reference line L1 does not necessarily pass through the barycentric position CP of the second area but at least passes through the second area.

The angle adjuster 74 performs an equal angular magnification process (angle maintaining process) (for the signal ratio space). In the equal angular magnification process (for the signal ratio space), an angle θ within a predetermined region R1x, which includes the first reference line L1, is maintained unchanged based on the angle change rate W1x. Here, an angle θ is defined by an angle from the first reference line L1. The angle θ is defined as a positive angle in the clockwise direction from the first reference line L1 and defined as a negative angle in the counterclockwise direction from the first reference line L1. The region R1x includes the angle θ ranging from "−θ1", which is less than "0", to "+θ2", which is greater than "0". In a case where the angle θ is within a region R1y, which is located outside the region R1x, the angle adjuster 74 performs an angle expansion process or an angle compression process. In the case of the angle expansion process, the angle θ is changed based on an angle change rate W1y that is greater than the angle change rate W1x. In the case of the angle compression process, the angle θ is changed based on an angle change rate W1y that is less than the angle change rate W1x. The region R1y includes a negative angle range from "−θ3", which is less than "−θ1", to "−θ1" and a positive angle range from "+θ2" to "+θ4", which is greater than "+θ2".

Figure 6:
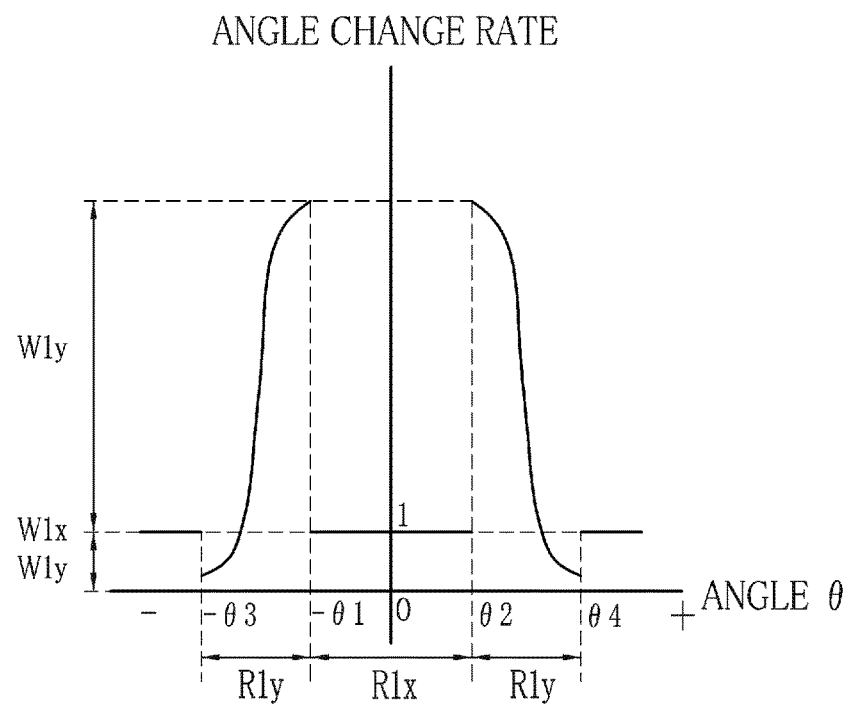
FIG. 6 is a graph illustrating a relationship between angle θ and angle change rate.

As illustrated in FIG. 6, the angle change rate W1x for an angle θ within the region R1x, in which the equal angular magnification process (for the signal ratio space) is to be performed, is set to 1.0. Thereby the angle θ before the equal angular magnification process is equivalent to the angle θ after the equal angular magnification process in the region R1x. The angle change rate W1y for an angle θ within the region R1y, in which the angle expansion process or the angle compression process is to be performed, is set to greater than or less than 1.0. Thereby the angle θ is changed by the angle expansion process or the angle compression process. In the positive angle range of the region R1y, the angle change rate W1y is the highest and greater than 1.0 in the case where the angle θ is "+θ2" and the angle change rate W1y decreases as the angle θ increases. The angle change rate W1y falls below 1.0 when the angle θ exceeds a predetermined value. In the negative angle range of the region R1y, the angle change rate W1y is the highest and greater than 1.0 in the case where the angle θ is "−θ1" and the angle change rate W1y decreases as the angle θ decreases. The angle change rate W1y falls below 1.0 when the angle θ falls below a predetermined value. Note that the angle change rate is set to 1.0 in the case where the angle θ is greater than "θ4" or less than "−θ3".

Figure 7:
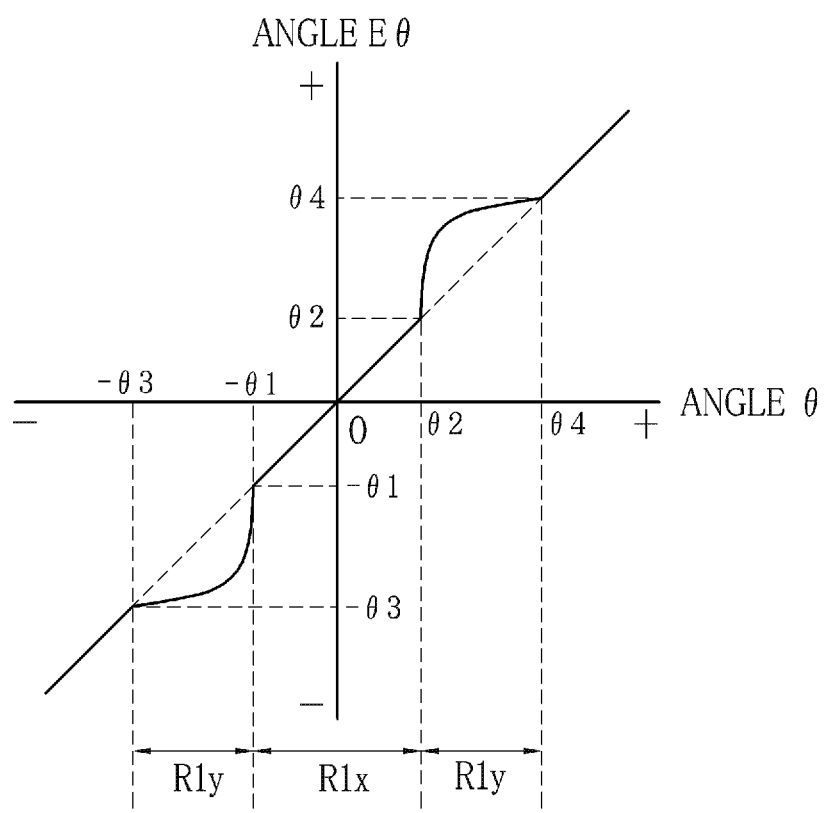
FIG. 7 is a graph illustrating a relationship between angles θ and Eθ.

As illustrated in FIG. 7, the angle θ in the region R1x is changed to the angle Eθ that is equivalent to the angle θ (Eθ=θ) through the equal angular magnification process (for the signal ratio space). Also in the case where the angle θ is greater than "θ4" or less than "−θ3", the angle θ is changed to the angle Eθ that is equivalent to the angle θ (Eθ=θ). In the case where the angle θ is in the positive angle range of the region R1y, the angle θ is changed to the positive angle Eθ that is greater than or equal to the angle θ (Eθ≥θ) through the angle expansion process or the angle compression process (for the signal ratio space). In the positive angle range, an amount (Eθ−θ) of the increase in angle in a range in which the angle change rate W1y is greater than 1.0 is greater than an amount (Eθ−θ) of the increase in angle in a range in which the angle change rate W1y is less than 1.0. In the case where the angle θ is in the negative angle range of the region R1y, the angle θ is changed to the negative angle Eθ that is less than or equal to the angle θ (Eθ≤θ) through the angle expansion process or the angle compression process. In the negative angle range, an amount (Eθ−θ) of the reduction in angle in a range in which the angle change rate W1y is greater than 1.0 is greater than an amount (Eθ−θ) of the reduction in angle in a range in which the angle change rate W1y is less than 1.0.

The following operation and effect are obtained by changing the angles. As illustrated in a part (A) of FIG. 8, the first area (B), the second area (C), and the third area (A) are close to each other before the equal angular magnification process and the angle expansion process or the angle compression process (for the signal ratio space). As illustrated in a part (B) of FIG. 8, after the equal angular magnification process and the angle expansion process or the angle compression process (for the signal ratio space), most of the coordinates corresponding to the first area (B) are moved in the clockwise direction with respect to the first reference line L1 and most of the coordinates corresponding to the third area (A) are moved in the counterclockwise direction with respect to the first reference line L while the position of the second area (C) is maintained unchanged in the signal ratio space. Thereby, the differences in hue among the first area (B), the second area (C), and the third area (A) are increased.

The special image, which is produced by increasing the differences in hue among the first area (B), the second area (C), and the third area (A), clearly displays the differences in color of the object among the portion infected with the *H. pylori*, the portion in which the eradication of the *H. pylori* infection has been successful, and the portion uninfected with the *H. pylori*.

Hereinafter, a process for adjusting the radial coordinate r, which is performed by the radial-coordinate adjuster 75, is described. As illustrated in FIG. 9, in a signal ratio space after the equal angular magnification process and the angle expansion process or the angle compression process, the first area, the second area, and the third area (denoted as "A") are apart from each other in the angle direction. A second reference line L2 passes through the barycentric position CP in the second area such that the second reference line L2 intersects the first reference line L1. The first area is located in the outside with respect to the second reference line L2. The third area is located in the inside with respect to the second reference line L2. Note that the second reference line L2 does not necessarily pass through the barycentric position CP of the second area but at least passes through the second area.

In a case where a radial coordinate r is in a predetermined region R2x, which includes the second reference line L2, the radial-coordinate adjuster 75 performs an equal radial-coordinate magnification process (a radial-coordinate maintaining process) (for the signal ratio space). In the equal radial-coordinate magnification process, the radial coordinate r is maintained unchanged based on the radial-coordinate change rate W2x. The region R2x includes the radial coordinates r ranging from "r1", which is less than "rc" corresponding to the second reference line L2, to "r2", which is greater than "rc". In a case where the radial coordinate r is within a region R2y, which is located outside the region R2x, the radial-coordinate adjuster 75 performs a radial-coordinate expansion process or a radial-coordinate compression process. In the case of the radial-coordinate expansion process, the radial coordinate r is changed based on a radial-coordinate change rate W2y that is greater than the radial-coordinate change rate W2x. In the case of the radial-coordinate compression process, the radial coordinate r is changed based on a radial-coordinate change rate W2y that is less than the radial-coordinate change rate W2x. The region R2y includes a small radial-coordinate range and a large radial-coordinate range. The small-coordinate range is from "r3", which is less than "r1", to "r1". The large radial-coordinate range is from "r2" to "r4", which is greater than "r2".

As illustrated in FIG. 10, in the case where the radial coordinate r is in the region R2x, in which the equal radial-coordinate magnification process (for the signal ratio space) is to be performed, the radial-coordinate change rate W2x is set to 1.0. Thereby the radial coordinate r before the equal radial-coordinate magnification process is equivalent to the radial coordinate r after the equal radial-coordinate magnification process in the region R2x. The radial-coordinate change rate W2y for a radial-coordinate r within the region R2y, in which the radial-coordinate expansion process or the radial-coordinate compression process is to be performed, is set to greater than or less than 1.0. Thereby the radial-coordinate r is changed by the radial-coordinate expansion process or the radial-coordinate compression process. In the small radial-coordinate range of the region R2y, the radial-coordinate change rate W2y is the highest and greater than 1.0 in the case where the radial-coordinate r is "r1" and the radial-coordinate change rate W2y decreases as the radial-coordinate r decreases. The radial-coordinate change rate W2y falls below 1.0 when the radial-coordinate r falls below a predetermined value. In the large radial-coordinate range of the region R2y, the radial-coordinate change rate W2y is the highest and greater than 1.0 in the case where the radial-coordinate r is "r2" and the radial-coordinate change rate W2y decreases as the radial-coordinate r increases. The radial-coordinate change rate W2y falls below 1.0 when the radial-coordinate r exceeds a predetermined value. Note that the radial-coordinate change rate is set to 1.0 in the case where the radial-coordinate r is greater than "r4" or less than "r3".

As illustrated in FIG. 11, the radial coordinate r in the region R2x is changed to the radial coordinate Er that is equivalent to the radial coordinate r (Er=r) through the equal radial-coordinate magnification process (for the signal ratio space). Also in the case where the radial coordinate r is greater than "r4" or less than "r3", the radial coordinate r is changed to the radial coordinate Er that is equivalent to the radial coordinate r (Er=r). In the case where the radial coordinate r is in the small radial-coordinate range of the region R2y, the radial coordinate r is changed to the radial coordinate Er that is less than or equal to the radial coordinate r (Er≤r) through the radial-coordinate expansion process or the radial-coordinate compression process. In the small radial-coordinate range, an amount (Er−r) of the reduction in radial coordinate in a range in which the radial-coordinate change rate W2y is greater than 1.0 is greater than an amount (Er−r) of the reduction in radial-coordinate in a range in which the radial-coordinate change rate W2y is less than 1.0. In the case where the radial coordinate r is in the large radial-coordinate range of the region R2y, the radial coordinate r is changed to the radial coordinate Er that is greater than or equal to the radial coordinate r (Er≥r) through the radial coordinate expansion process or the radial coordinate compression process. In the large radial-coordinate range, an amount (Er−r) of the increase in radial coordinate in a range in which the radial-coordinate change rate W2y is greater than 1.0 is greater than an amount (Er−r) of the increase in radial coordinate in a range in which the radial-coordinate change rate W2y is less than 1.0.

The following operation and effect are obtained by changing the radial coordinates. As illustrated in a part (A) of FIG. 12, before the equal radial-coordinate magnification process and the radial-coordinate expansion process or the radial-coordinate compression process, the first area (B), the second area (C), and the third area (A) are apart from each other in the angle direction but close to each other in the radial-coordinate direction. As illustrated in a part (B) of FIG. 12, after the equal radial-coordinate magnification process and the radial-coordinate expansion process or the radial-coordinate compression process (for the signal ratio space), most of the coordinates corresponding to the first area (B) are moved outwardly away from the second reference line L2 and most of the coordinates corresponding to the third area (A) are moved inwardly away from the second reference line L2 while the position of the second area (C) is maintained unchanged in the signal ratio space. Thereby the differences in saturation among the first area (B), the second area (C), and the third area (A) are increased.

As described above, the differences in saturation are increased among the first area (B), the second area (C), and the third area (A) in addition to the differences in hue. Thus, the special image clearly displays the differences in color of the object among the portion infected with the *H. pylori*, the portion in which the eradication of the *H. pylori* infection has been successful, and the portion uninfected with the *H. pylori*.

Hereinafter, referring to a flowchart in FIG. 13, a procedure of the observation of the object in the special mode is described. First, the observation mode is set to the normal mode. The insertion section 12a of the endoscope 12 is inserted into the body cavity. After the distal end portion 12d of the insertion section 12a reaches the stomach, the mode SW 13a is operated to switch from the normal mode to the special mode.

The signal ratio calculator 72 calculates the B/G ratio and the G/R ratio based on the RGB image signals obtained after the observation mode is switched to the special mode. Then, the B/G ratio and the G/R ratio are converted into the radial coordinate r and the angle θ through the polar coordinate conversion.

Next, the angle adjuster 74 performs the equal angular magnification process and the angle expansion process or the angle compression process. In the equal angular magnification process, an angle in the region R1x, which includes the first reference line L1 passing through the barycentric position CP of the second area, is maintained unchanged. An angle in the region R1y, which is located outside the region R1X, is expanded or compressed through the angle expansion process or the angle compression process. As a result of the equal angular magnification process and the angle expansion process or the angle compression process, the first area is rotationally moved away from the first reference line L1 in the clockwise direction and the third area is rotationally moved away from first reference line L1 in the counterclockwise direction while the position of the second area is maintained unchanged in the signal ratio space. Thereby the differences in hue among the first area, the second area, and the third area are increased.

After the angle adjustment is finished, the radial-coordinate adjuster 75 performs the equal radial-coordinate magnification process and the radial-coordinate expansion process or the radial-coordinate compression process. In the equal radial-coordinate magnification process, a radial-coordinate in the region R2x is maintained unchanged. The region R2x includes the second reference line L2, which passes through the barycentric position CP of the second area and intersects the first reference line L1. A radial-coordinate in the region R2y, which is located outside the region R2x, is expanded or compressed through the radial-coordinate expansion process or the radial-coordinate compression process. As a result of the equal radial-coordinate magnification process and the radial-coordinate expansion process or the radial-coordinate compression process, the first area is moved outwardly with respect to the second reference line L2 and the third area is moved inwardly with respect to the second reference line L2 while the position of the second area is maintained unchanged in the signal ratio space.

As a result of the angle adjustment and the radial-coordinate adjustment described above, as illustrated in FIG. 14, the first area (B) and the third area (A) are moved in directions different from each other in each of saturation direction and hue direction while the position of the second area (c) is maintained unchanged in the HS space formed by H (hue) and S (saturation). Thus, the differences in saturation are increased among the first area, the second area, and the third area in addition to the differences in hue. The special image is produced based on the radial coordinates r and the angles θ with the differences in hue and saturation among the first to third areas increased. The special image is displayed on the monitor 18. In FIG. 14, note that the areas depicted with dotted lines are those before the angle adjustment and the radial-coordinate adjustment. The areas depicted with solid lines are those after the angle adjustment and the radial-coordinate adjustment.

Embodiment 1B

In the above embodiment 1A, the signal ratio calculator 72 calculates the B/G ratio and the G/R ratio from the first RGB image signals. In the feature space formed by the B/G ratio and the G/R ratio, "the equal angular magnification process and the angle expansion process or the angle compression process" and "the equal radial-coordinate magnification process and the radial-coordinate expansion process or the radial-coordinate compression process" are performed. In an embodiment 1B, chrominance signals Cr and Cb are obtained as the color information. In a feature space formed by the chrominance signals Cr and Cb, "the equal angular magnification process and the angle expansion process or the angle compression process" and "the equal radial-coordinate magnification process and the radial-coordinate expansion process or the radial-coordinate compression process" are performed.

In the embodiment 1B, a special image processor 92 (see FIG. 15) is used. Unlike the special image processor 64, the special image processor 92 is not provided with the log converter 71, the signal ratio calculator 72, and the inverse log converter 79. Instead, the special image processor 92 comprises a luminance/chrominance signal converter 85 between the inverse gamma converter 70 and the polar coordinate converter 73. The components, other than those described above, of the special image processor 92 are the same as or similar to the components of the special image processor 64.

The luminance/chrominance signal converter 85 (which corresponds to the color information obtaining section of the present invention, for example) converts the first RGB image signals into a luminance signal Y and the chrominance signals Cr and Cb. A well-known conversion equation is used for the conversion into the chrominance signals Cr and Cb. The chrominance signals Cr and Cb are transmitted to the polar coordinate converter 73. The luminance signal Y is transmitted to the RGB converter 77 and the brightness adjuster 81. The RGB converter 77 converts the chrominance signals Cr and Cb, which passed through the Cartesian coordinate converter 76, and the luminance signal Y into the second RGB image signals. The brightness adjuster 81 adjusts the pixel values of the second RGB image signals with the use of the luminance signal Y (the first brightness information Yin) and the second brightness information (the second brightness information Yout), which is calculated by the second brightness information calculator 81*b*. Note that the method for calculating the second brightness information Yout and the method for adjusting the pixel values of the second RGB image signals are the same as or similar to those of the special image processor 64.

In a feature space (hereinafter referred to as the Cb-Cr space) formed by the chrominance signal Cr (the vertical axis) and the chrominance signal Cb (the horizontal axis), the special image processor 92 performs "the equal angular magnification process and the angle expansion process or the angle compression process" and "the equal radial-coordinate magnification process and the radial-coordinate expansion process or the radial-coordinate compression process" (for the Cb-Cr space). In the Cb-Cr space, as illustrated in FIG. 16, all of the first to third areas (denoted as B, C, and A, respectively) are located in the second quadrant of the Cb-Cr space. The third area (A) is closest to the vertical axis Cr. The second area (C) is second closest to the vertical axis Cr. The first area (B) is farthest from the vertical axis Cr.

As illustrated in FIG. 17, the equal angular magnification process and the angle expansion process or the angle compression process (for the Cb-Cr space), which are performed by the angle adjuster 74, are substantially similar to the equal angular magnification process and the angle expansion process or the angle compression process (for the signal ratio space). An angle in the region R1x, which includes the first reference line L1 passing through the barycentric position CP of the second area, is maintained unchanged. An angle in the region R1y, which is located outside the region R1x, is expanded or compressed significantly. Thereby the first area (B) is moved away from the first reference line L1 in the counterclockwise direction and the third area (A) is moved away from the first reference line L1 in the clockwise direction while the position of the second area (C) is maintained unchanged in the Cb-Cr space. Thereby the differences in hue among the first area (B), the second area (C), and the third area (A) are increased. In FIG. 17, note that the areas depicted with dotted lines are those before the angle expansion or the angle compression (for the Cb-Cr space). The areas depicted with solid lines are those after the angle expansion or the angle compression (for the Cb-Cr space). The same applies to FIG. 18.

As illustrated in FIG. 18, an equal radial-coordinate magnification process and a radial-coordinate expansion process or a radial-coordinate compression process (for the Cb-Cr space), which are performed by the radial-coordinate adjuster 75, are substantially similar to the equal radial-coordinate magnification process and the radial-coordinate expansion process or the radial-coordinate compression process (for the signal ratio space). In the equal radial-coordinate magnification process, a radial coordinate in the region R1x, which includes the second reference line L2 passing through the barycentric position CP of the second area and intersecting the first reference line L1, is maintained unchanged. A radial coordinate in the region R1y, which is located outside the region R1x, is expanded or compressed significantly. Thereby the first area (B) is moved outwardly away from the second reference line L2 and the third area (A) is moved inwardly away from the second reference line L2 while the position of the second area (C) is maintained unchanged in the Cb-Cr space. Thus, the differences in hue and saturation among the first area (B), the second area (C), and the third area (A) are increased.

Embodiment 1C

In an embodiment 1C, a lab converter (which corresponds to the color information obtaining section of the present invention, for example) performs lab conversion of the first RGB image signals to obtain a* and b* (that is, the color components a* and b* (the color information in this embodiment) of CIE lab space, and the same applies to the following). In a feature space (ab space) formed by a* and b*, "the equal angular magnification process and the angle expansion process or the angle compression process" and "the equal radial-coordinate magnification process and the radial-coordinate expansion process or the radial-coordinate compression process" are performed. Note that CIE Lab refers to a color system defined by CIE (Commission internationale de l'éclairage or International Commission on Illumination).

In this embodiment, a special image processor 82 (see FIG. 19) is used. Unlike the special image processor 64, the special image processor 82 is not provided with the inverse gamma converter 70, the log converter 71, the signal ratio calculator 72, the inverse log converter 79, and the gamma converter 80. Instead, the special image processor 82 comprises a Lab converter 83, which is an example of the color information obtaining section of the present invention. The components, other than those described above, of the special image processor 82 are the same as or similar to the components of the special image processor 64.

The Lab converter 83 converts the first RGB image signals into L, a*, and b* through the well-known Lab conversion. "L" is transmitted to the RGB converter 77 and the brightness adjuster 81, and "a*" and "b*" are transmitted to the polar coordinate converter 73. The RGB converter 77 converts "a*" and "b*", which have passed through the Cartesian coordinate converter 76, and "L" into the second RGB image signals. The first brightness information calculator 81a of the brightness adjuster 81 converts "L", which is transmitted from the Lab converter 83, into the luminance signal Y with the use of a predetermined conversion equation. The converted luminance signal Y is referred to as the first brightness information Yin. The second brightness information calculator 81b calculates the second brightness information Yout from the second RGB image signals. The brightness adjuster 81 uses the first brightness information Yin and the second brightness information Yout to adjust the pixel values of the second RGB image signals. Note that the method for calculating the second brightness information Yout and the method for adjusting the pixel values of the second RGB image signals are the same as or similar to those of the special image processor 64.

Embodiment 2

In an embodiment 2, a laser and a phosphor are used, instead of the LEDs 20a to 20d of the four colors described in the embodiments 1A to 1C, to illuminate the object. Other than those, the configuration is the same as or similar to that of the embodiments 1A to 1C.

As illustrated in FIG. 22, in the light source device 14 of an endoscope system 100 according to the embodiment 2, a blue laser (denoted as 445LD in FIG. 22) 104 and a blue-violet laser (denoted as 405LD in FIG. 22) 106 are provided in place of the LEDs 20a to 20d of the four colors. The blue laser 104 emits blue laser beams with the center wavelength 445±10 nm. The blue-violet laser 106 emits blue-violet laser beams with the center wavelength 405±10 nm. The light emissions from the semiconductor light emitting elements of the lasers 104 and 106 are controlled individually by a source controller 108. The light quantity ratio between the light (laser beams) from the blue laser 104 and the light (laser beams) from the blue-violet laser 106 is changed as desired.

In the normal mode, the source controller 108 actuates the blue laser 104. In the special mode, the source controller 108 actuates both the blue laser 104 and the blue-violet laser 106 such that the light-emission ratio of the blue laser beams is greater than that of the blue-violet laser beams. The laser beams emitted from each of the lasers 104 and 106 are incident on the light guide (LG) 41 through optical members (e.g. a condenser lens, an optical fiber, a combiner, and the like, all not shown).

Note that the full width at half maximum of the blue laser beams or the blue-violet laser beams is preferred to be in the order of ±10 nm. Broad-area type InGaN-based laser diodes, InGaNAs-based laser diodes, and/or GaNAs-based laser diodes may be used for the blue laser 104 and blue-violet laser 106. A light emitting element such as a light emitting diode may be used as the light source.

The illumination optical system 30a is provided with the light lens 45 and a phosphor 110 on which the blue laser beams or the blue-violet laser beams from the light guide 41 are incident. The blue laser beams causes the phosphor 110 to emit fluorescence. A part of the blue laser beams passes through the phosphor 110. The blue-violet laser beams pass through the phosphor 110 without exciting the phosphor. The light from the phosphor 110 is applied to the object through the light lens 45.

Here, in the normal mode, the blue laser beams are mostly incident on the phosphor 110, so that the white light, which is the combination of the blue laser beams and the fluorescence from the phosphor 110 excited by the blue laser beams, is applied to the object as illustrated in FIG. 23. In the special mode, both the blue-violet laser beams and the blue laser beams are incident on the phosphor 110, so that the special light, which is the combination of the blue-violet laser beams, the blue laser beams, and the fluorescence from the phosphor 110 excited by the blue laser beams, is applied to the object as illustrated in FIG. 24.

Note that it is preferred to use the phosphor 110 containing two or more types of phosphor components (e.g. YAG-based phosphor, $BAM(BaMgAl_{10}O_{17})$, or the like) that absorb a part of the blue laser beams and emit light of green to yellow. In the case where the semiconductor light emitting elements are used as the excitation light sources for the phosphor 110 as described in this example, the high-intensity white light is provided with high light-emission efficiency, the intensity of the white light is controlled easily, and the variations in the color temperature and chromaticity of the white light are small.

Embodiment 3

In an embodiment 3, instead of the LEDs 20a to 20d of the four colors described in the embodiments 1A to 1C, a broadband light source (e.g. a xenon lamp) and a rotary filter are used to illuminate the object. Instead of the color image sensor 48, a monochrome image sensor is used to capture the images of the object. The components other than those are the same as or similar to the components described in the embodiments 1A to 1C.

As illustrated in FIG. 25, in an endoscope system 200 of the embodiment 3, a broadband light source 202, a rotary filter 204, and a filter switcher 205 are provided instead of the LEDs 20a to 20d in the light source device 14. The imaging optical system 30b is provided with a monochrome image sensor 206 with no color filter, in place of the color image sensor 48.

The broadband light source 202 is composed of a xenon lamp, a white LED, or the like, and emits the white light in the wavelength range from blue to red. The rotary filter 204 comprises a normal filter 208 provided on the inner side and a special filter 209 provided on the outer side (see FIG. 26). The normal filter 208 is used in the normal mode. The special filter 209 is used in the special mode. The filter switcher 205 shifts the rotary filter 204 in the radial direction. In a case where the observation mode is set to the normal mode by the operation of the mode SW 13a, the filter switcher 205 inserts the normal filter 208 of the rotary filter 204 into the light path of the white light. In a case where the observation mode is set to the special mode, the filter switcher 205 inserts the special filter 209 of the rotary filter 204 into the light path of the white light.

As illustrated in FIG. 26, the normal filter 208 comprises a B filter 208a, a G filter 208b, and an R filter 208c in a circumferential direction. The B filter 208a transmits the blue light of the white light. The G filter 208b transmits the green light of the white light. The R filter 208c transmits the red light of the white light. In the normal mode, the blue light, the green light, and the red light are applied in this order to the object as the rotary filter 204 is rotated.

The special filter 209 comprises a Bn filter 209a, a G filter 209b, and an R filter 209c in the circumferential direction. The Bn filter 209a transmits blue narrowband light in a specific wavelength range of the white light. The G filter 209b transmits the green light of the white light. The R filter 209c transmits the red light of the white light. In the special mode, the blue narrowband light, the green light, and the red light are applied in this order to the object as the rotary filter 204 is rotated.

In the endoscope system 200, in the normal mode, the monochrome image sensor 206 captures an image of the object every time the blue light, the green light, or the red light is applied to the object. Thereby, the three colors (RGB) of image signals are obtained. The normal image is produced based on the RGB image signals in a manner the same as or similar to those in the embodiments 1A to 1C.

In the special mode, the image sensor 206 captures an image of the object every time the blue narrowband light, the green light, or the red light is applied to the object. Thereby, the Bn image signal, the G image signal, and the R image signal are obtained. The special image is produced based on the Bn image signal, the G image signal, and the R image signal. The Bn image signal is used in place of the B image signal to produce the special image. Other than that, the special image is produced in a manner the same as or similar to those of the embodiments 1A to 1C.

Embodiment 4

In an embodiment 4, a capsule endoscope, which is to be swallowed by a patient, is used in place of the insertion-type endoscope 12 and the light source device 14. The RGB image signals necessary for producing a normal image or a special image are obtained from the capsule endoscope.

As illustrated in FIG. 27, a capsule endoscope system 300 according to the embodiment 4 comprises a capsule endoscope 302, a transmission/reception antenna 304, a receiving device 306 for the capsule endoscope 302, the processor device 16, and the monitor 18. The capsule endoscope 302 comprises LEDs 302a, an image sensor 302b, an image processor 302c, and a transmission antenna 302d. Note that the processor device 16 is the same as or similar to the ones used in the embodiments 1A to 1C. In the embodiment 4, a mode switch (SW) 308 is provided to switch between the normal mode and the special mode.

Inside the capsule endoscope 302, two or more LEDs 302a that emit white light are provided. Here, it is preferred that the LED 302a is a white light LED which comprises a blue light source and a phosphor which converts the light from the blue light source into fluorescence. An LD (laser diode) may be used instead of the LED. The object is illuminated with the white light from the LEDs 302a.

The image sensor 302b is a color image sensor. The image sensor 302b captures an image of the object illuminated with the white light and outputs the RGB image signals. Here, it is preferred that the image sensor 302b is a CCD (Charge Coupled Device) image sensor or a CMOS (Complementary Metal-Oxide Semiconductor) image sensor. The image processor 302c performs a process to convert the RGB image signals, which are outputted from the image sensor 302b, into signals to be transmitted through the transmission antenna 302d. The RGB image signals, which have passed through the image processor 302c, are transmitted wirelessly from the transmission antenna 302d to the transmission/reception antenna 304.

The transmission/reception antenna 304 is affixed to the subject's body, and receives the RGB image signals from the transmission antenna 302d. The transmission/reception antenna 304 wirelessly transmits the received RGB image signals to the receiving device 306 for the capsule endoscope 302. The receiving device 306 is connected to the receiver 53 of the processor device 16, and transmits the RGB image signals from the transmission/reception antenna 304 to the receiver 53.

Note that, in the above embodiments, the four colors of light with the emission spectra illustrated in FIG. 3 are used by way of example. The emission spectra are not limited to this example. For example, as illustrated in FIG. 28, the green light G and the red light R may have the same spectra as those illustrated in FIG. 3. The violet light Vs may have the center wavelength 410 to 420 nm in a wavelength range slightly shifted to a longer wavelength side than that of the violet light V in FIG. 3. The blue light Bs may have the center wavelength 445 to 460 nm in a wavelength range slightly shifted to a shorter wavelength side than that of the blue light B in FIG. 3.

Note that, in the above embodiments, the B/G ratio and the G/R ratio are converted into the radial coordinate r and the angle θ through the polar coordinate conversion. Then "the equal angular magnification process and the angle expansion process or the angle compression process" and "the equal radial-coordinate magnification process and the radial-coordinate expansion process or the radial-coordinate compression process" are performed. Thereafter, the radial coordinate r and the angle θ are converted back into the B/G ratio and the G/R ratio. Alternatively, as illustrated in FIG. 29, a two-dimensional LUT 400 may be used to directly convert the B/G and G/R ratios into the processed B/G and G/R ratios, which have been subjected to "the equal angular magnification process and the angle expansion process or the angle compression process" and "the equal radial-coordinate magnification process and the radial-coordinate expansion process or the radial-coordinate compression process", without the polar coordinate conversion.

Note that the two-dimensional LUT 400 stores the B/G and G/R ratios in association with the processed B/G and G/R ratios, which have been subjected to "the equal angular magnification process and the angle expansion process or the angle compression process" and "the equal radial-coordinate magnification process and the radial-coordinate expansion process or the radial-coordinate compression process", which are performed based on the B/G and G/R ratios. The first RGB image signals outputted from the inverse gamma converter 70 are inputted to the two-dimensional LUT 400 or the RGB converter 77.

In the above embodiment, the equal radial-coordinate magnification process and the radial-coordinate expansion process or the radial-coordinate compression process are performed after the equal angular magnification process and the angle expansion process or the angle compression process. Note that the equal radial-coordinate magnification process and the radial-coordinate expansion process or the radial-coordinate compression process may be performed prior to the equal angular magnification process and the angle expansion process or the angle compression process.

Note that the present invention is applicable to various types of medical image processing devices in addition to the processor devices incorporated the endoscope systems described in the embodiments 1 to 3 and the capsule endoscope system described in the embodiment 4.

Various changes and modifications are possible in the present invention and may be understood to be within the present invention.

What is claimed is:

1. A medical image processing device comprising:
a processing circuitry configured to:

perform an input process of a first color image signal obtained by capturing a reflection image of an object illuminated by illumination light of two or more colors;

obtain two or more pieces of color information from the first color image signal, the two or more pieces of color information being included in one of first, second, and third areas in a feature space formed by the two or more pieces of color information, according to a condition of the object;

perform an equal angular magnification process and an angle expansion process or an angle compression process in the feature space, an angle in a region R1x including a first reference line passing through the second area being maintained unchanged based on an angle change rate W1x in the equal angular magnification process, an angle in a region R1y located outside the region R1x being changed based on an angle change rate W1y greater than the angle change rate W1x in the angle expansion process or based on an angle change rate W1y less than the angle change rate W1x in the angle compression process;

perform an equal radial-coordinate magnification process and a radial-coordinate expansion process or a radial-coordinate compression process in the feature space, a radial coordinate in a region R2x including a second reference line passing through the second area and intersecting the first reference line being maintained unchanged based on a radial-coordinate change rate W2x in the equal radial-coordinate magnification process, a radial coordinate in a region R2y located outside the region R2x being changed based on a radial-coordinate change rate W2y greater than the radial-coordinate change rate W2x in the radial-coordinate expansion process or based on a radial-coordinate change rate W2y less than the radial-coordinate change rate W2x in the radial-coordinate compression process; and generate a medical image based on the two or more pieces of color information after subjected to the equal angular magnification process and the angle expansion process or the angle compression process, and the equal radial-coordinate magnification process and the radial-coordinate expansion process or the radial-coordinate compression process.

2. The medical image processing device according to claim 1, wherein each of the angle change rate W1x and the radial-coordinate change rate W2x is 1.0.

3. The medical image processing device according to claim 1, wherein the angle expansion process or the angle compression process changes each of the angle in the area in the region R1y on one side of the first reference line and the angle in the another area in the region R1y on the other side of the first reference line to be away from the first reference line in an angle direction.

4. The medical image processing device according to claim 1, wherein in a case where an angle $\theta$ is defined as an angle from the first reference line, and the angle $\theta$ located on one side of the first reference line is defined as a positive angle and the angle $\theta$ located on the other side of the first reference line is defined as a negative angle, the region R1x is a range in which the angle $\theta$ ranges from "$-\theta1$" that is less than "0" to "$+\theta2$" that is greater than "0", and the angle $\theta$ before the equal angular magnification process is equivalent to the angle $\theta$ after the equal angular magnification process in the region R1x, and the region R1y includes a negative angle range in which the angle $\theta$ ranges from "$-\theta3$" that is less than "$-\theta1$" to "$-\theta1$" and a positive angle range in which the angle $\theta$ ranges from "$\theta2$" to "$\theta4$" that is greater than "$\theta2$", and the angle $\theta$ after the angle expansion process or the angle compression process is less than the angle $\theta$ before the angle expansion process or the angle compression process in the negative angle range, and the angle $\theta$ after the angle expansion process or the angle compression process is greater than the angle $\theta$ before the angle expansion process or the angle compression process in the positive angle range.

5. The medical image processing device according to claim 4, wherein the processing circuitry maintains the angle $\theta$ unchanged based on the angle change rate W1x in a case where the angle $\theta$ is greater than "$\theta4$" or less than "$-\theta3$".

6. The medical image processing device according to claim 1, wherein the radial-coordinate expansion process or the radial-coordinate compression process changes each of the radial coordinate in the area in the region R2y on one side of the second reference line and the radial coordinate in the another area in the region R2y on the other side of the second reference line to be away from the second reference line in a radial-coordinate direction.

7. The medical image processing device according to claim 1, wherein in a case where the radial coordinate r corresponding to the first reference line is defined as a radial coordinate rc, the region R2x is a range in which the radial coordinate r ranges from "r1" that is less than "rc" to "r2" that is greater than "rc", and the radial coordinate r before the equal radial-coordinate magnification process is equivalent to the radial coordinate r after the equal radial-coordinate magnification process in the region R2x, and the region R2y comprises a small radial-coordinate range in which the radial coordinate r ranges from "r3" that is less than "r1" to "r1" and a large radial-coordinate range in which the radial coordinate r ranges from "r2" to "r4" that is greater than "r2", and the radial coordinate r after the radial-coordinate expansion or the radial-coordinate compression is less than the radial coordinate r before the radial-coordinate expansion or the radial-coordinate compression in the small radial-coordinate range, and the radial coordinate r after the radial-coordinate expansion or the radial-coordinate compression is greater than the radial coordinate r before the radial-coordinate expansion or the radial-coordinate compression in the large radial-coordinate range.

8. The medical image processing device according to claim 7, wherein the processing circuitry maintains the radial coordinate r unchanged based on the radial-coordinate change rate W2x in a case where the radial coordinate r is greater than "r4" or less than "r3".

9. The medical image processing device according to claim 1, wherein the first area is located on one side of the first reference line and the third area is located on the other side of the first reference line.

10. The medical image processing device according to claim 1, wherein the first area is located on one side of the second reference line and the third area is located on the other side of the second reference line.

11. The medical image processing device according to claim 1, wherein the first color image signal comprises image signals of three colors, and the two or more pieces of color information are a first signal ratio between the image signals of the two colors out of the three colors and a second signal ratio between the image signals of the two colors different from the first signal ratio, and the feature space is a signal ratio space formed by the first signal ratio and the second signal ratio.

12. The medical image processing device according to claim 1, wherein the feature space is any one of a Cb-Cr space formed by chrominance signals Cr and Cb, which correspond to the two or more pieces of color information, and an ab space formed by color components a* and b*, which correspond to the two or more pieces of color information, of CIE Lab space.

13. The medical image processing device according to claim 1, wherein the second area maintains its position in an HS space formed by H (hue) and S (saturation) and the first and third areas move in directions different from each other in each of a hue direction and a saturation direction in the HS space, through the equal angular magnification process and the angle expansion process or the angle compression process, and the equal radial-coordinate magnification process and the radial-coordinate expansion process or the radial-coordinate compression process.

14. The medical image processing device according to claim 1, further comprising:
   a color image signal converter configured to convert the two or more pieces of color information that have been subjected to the equal angular magnification process and the angle expansion process or the angle compression process and the equal radial-coordinate magnification process and the radial-coordinate expansion process or the radial-coordinate compression process into a second color image signal; and
   a brightness adjuster for adjusting a pixel value of the second color image signal based on first brightness information calculated from the first color image signal and second brightness information calculated from the second color image signal.

15. A method of processing a medical image comprising the steps of:
   performing an input process of a first color image signal obtained by capturing a reflection image of an object illuminated by illumination light of two or more colors with a processing circuitry;
   obtaining two or more pieces of color information from the first color image signal, the two or more pieces of color information being included in one of first, second, and third areas in a feature space formed by the two or more pieces of color information, according to a condition of the object, with the processing circuitry;
   performing an equal angular magnification process and an angle expansion process or an angle compression process with the processing circuitry in the feature space, an angle in a region R1x including a first reference line passing through the second area being maintained unchanged based on an angle change rate W1x in the equal angular magnification process and an angle in a region R1y located outside the region R1x being changed based on an angle change rate W1y greater than the angle change rate W1x in the angle expansion process or based on an angle change rate W1y less than the angle change rate W1x in the angle compression process;
   performing an equal radial-coordinate magnification process and a radial-coordinate expansion process or a radial-coordinate compression process in the feature space with the processing circuitry, a radial coordinate in a region R2x including a second reference line passing through the second area and intersecting the first reference line being maintained unchanged based on a radial-coordinate change rate W2x in the equal radial-coordinate magnification process, a radial coordinate in a region R2y located outside the region R2x being changed based on a radial-coordinate change rate W2y greater than the radial-coordinate change rate W2x in the radial-coordinate expansion process or based on a radial-coordinate change rate W2y less than the radial-coordinate change rate W2x in the radial-coordinate compression process; and
   generating a medical image based on the two or more pieces of color information after subjected to the equal angular magnification process and the angle expansion process or the angle compression process, and the equal radial-coordinate magnification process and the radial-coordinate expansion process or the radial-coordinate compression process.

\* \* \* \* \*